(12) United States Patent
Kawahara et al.

(10) Patent No.: US 7,662,345 B2
(45) Date of Patent: Feb. 16, 2010

(54) FLUID HANDLING APPARATUS AND FLUID HANDLING UNIT FOR USE THEREIN

(75) Inventors: Noriyuki Kawahara, Saitama (JP); Takuhito Ohse, Saitama (JP); Kyouhei Yamada, Saitama (JP); Satoshi Ikeya, Kawaguchi (JP)

(73) Assignee: Enplas Corporation, Saitama (JP)

( * ) Notice: Subject to any disclaimer, the term of this patent is extended or adjusted under 35 U.S.C. 154(b) by 510 days.

(21) Appl. No.: 11/717,926

(22) Filed: Mar. 13, 2007

(65) Prior Publication Data

US 2007/0217955 A1    Sep. 20, 2007

(30) Foreign Application Priority Data

Mar. 16, 2006   (JP)   ............................. 2006-072781
Dec. 14, 2006   (JP)   ............................. 2006-336588

(51) Int. Cl.
*B01L 11/00* (2006.01)
*G01N 33/00* (2006.01)
*B01L 3/00* (2006.01)
*C12M 1/34* (2006.01)

(52) U.S. Cl. ..................... 422/101; 422/68.1; 422/99; 422/102; 435/287.2; 435/287.9; 435/288.4

(58) Field of Classification Search ................. 422/58, 422/61, 101, 59, 69, 102; 210/261
See application file for complete search history.

(56) References Cited

U.S. PATENT DOCUMENTS

| | | | | |
|---|---|---|---|---|
| 4,425,438 | A | * | 1/1984 | Bauman et al. ............. 436/527 |
| 5,650,125 | A | * | 7/1997 | Bosanquet .................. 422/102 |
| 6,576,460 | B1 | * | 6/2003 | Baeumner et al. ........ 435/287.1 |
| 7,001,774 | B1 | * | 2/2006 | Gamble et al. ................ 436/54 |

FOREIGN PATENT DOCUMENTS

| | | |
|---|---|---|
| JP | 9-101302 | 4/1997 |
| JP | 9-159673 | 6/1997 |
| JP | 2001-4628 | 1/2001 |

* cited by examiner

*Primary Examiner*—Angela Ortiz
*Assistant Examiner*—Charles D Hammond
(74) *Attorney, Agent, or Firm*—Bachman & LaPointe, P.C.

(57) ABSTRACT

A fluid handling apparatus 10 has a plurality of fluid handling subassemblies 16 arrayed on a plate body 12. Each of the fluid handling subassemblies includes: an injecting section 26 for injecting a fluid; a fluidized section 28 for allowing the fluid to continuously flow downwards; a fluid housing chamber 30 for receiving the fluid from the fluidized section; a wall portion 20 formed between the fluid housing chamber and the fluidized section; slits 20b for allowing the fluid to enter the fluid housing chamber; and a surface-area increasing means 22 for increasing the area of a contact surface with the fluid in the fluidized section. The slits extend from a lower end positioned in the vicinity of the lower end of the fluidized section, to an upper end higher than the upper end of the fluidized section, for allowing the injecting section and fluidized section to be communicated with the fluid housing chamber.

16 Claims, 27 Drawing Sheets

FLUID HANDLING APPARATUS AND FLUID HANDLING UNIT FOR USE THEREIN

BACKGROUND OF THE INVENTION

1. Field of the Invention

The present invention generally relates to a fluid handling apparatus and a fluid handling unit for use therein. More specifically, the invention relates to a fluid handling apparatus capable of being used as a sample analyzing apparatus for analyzing samples, such as biosubstances representative of functional substances, and a fluid handling unit for use therein.

2. Description of the Prior Art

As conventional methods for specifically detecting biosubstances, such as proteins, there are known various methods for causing an antigen-antibody reaction using an antibody to a specific biosubstance, to carry out the visual recognition or spectroscopic measurement of a reactant thus obtained, to detect the biosubstance.

As methods for quantifying a reactant obtained by an antigen-antibody reaction of a biosubstance, such as a protein, there are widely adopted some methods, such as ELISA (Enzyme-Linked ImmunoSorbent Assay). In these methods, there is used a sample analyzing apparatus called a microplate wherein a large number of fine recessed portions generally called microwells (which will be hereinafter referred to as "wells") are arrayed. The wall surfaces of the wells are coated with an antibody to a specific biosubstance, which is a target substance, as a capturing (or catching) material, to capture (or catch) the target substance by the capturing material to detect the target substance by measuring a reactant, which is obtained by an antigen-antibody reaction between the target substance and the antibody, by fluorescence, luminous reagents or the like.

In a typical method using a microplate, such as ELISA, a well is filled with a liquid, such as a specimen containing a target substance or an antibody reagent, as a reaction solution to cause a reaction. This reaction does not occur until the components in the liquid filled in the well are moved by molecular diffusion to reach the bottom and inner walls of the well. For that reason, if a microplate is allowed to stand, a theoretical reaction time depends on the diffusion time of the components in the liquid filled in the well. Since the molecules in the liquid move while colliding with the surrounding molecules, the speed of diffusion is very slow. If the target substance is a protein having a molecular weight of about 70,000, the speed of diffusion is about 0.5 to $1 \times 10^{-6}$ cm$^2$/sec in a dilute aqueous solution (room temperature). Therefore, in the liquid filled in the well, the target substance located apart from the bottom and inner walls of the well is hardly allowed to react in a practical measuring time. In addition, since it is effective to cause the bottom and wall surfaces in the well serving as a reacting portion to uniformly contact the reaction solution in order to improve the efficiency of reaction in a microplate, it is required to use a larger quantity of liquid than the quantity of liquid required for the reaction.

Thus, in the conventional method using the microplate, such as ELISA, the antigen-antibody reaction proceeds only on the wall surface of the well coated with the capturing antibody. Therefore, the liquid must be allowed to stand until the reaction occurs after the target substance, antibody and substrate contained in the liquid fed into the well are suspended, circulated and sink to reach the wall surface of the well, so that there is a problem in that the efficiency of reaction is bad. In addition, in a microplate which is subdivided into a large number of wells, the quantity of liquid fed into each of the wells is limited, so that there is a problem in that the sensitivity of measurement is deteriorated.

In order to improve the sensitivity of measurement and shorten the measuring time in ELISA or the like, there is proposed a microplate capable of increasing the surface area of a reaction surface (capturing surface) to enhance the sensitivity of measurement by forming fine irregularities on the bottom face of each of wells serving as the reaction surface (see, e.g., Japanese Patent Laid-Open No. 9-159673). There is also proposed a microchip capable of increasing the surface area of a reaction surface to enhance the efficiency of reaction in a fine space by arranging a fine solid particle (bead) as a reaction solid phase in a microchannel of the microchip (see, e.g., Japanese Patent Laid-Open No. 2001-4628). Moreover, there is proposed a microplate capable of increasing the surface area of a reaction surface and saving the quantity of samples by forming a small-diameter recessed portion in the central portion of the bottom of each of wells. (see, e.g., Japanese Patent Laid-Open No. 9-101302).

However, in the microplate proposed in Japanese Patent Laid-Open No. 9-159673, there is a problem in that it is not possible to improve the efficiency of reaction although it is possible to improve the sensitivity of measurement. In addition, the microchip proposed in Japanese Patent Laid-Open No. 2001-4628 is not suitable for the measurement of a large number of specimens although it is possible to improve the efficiency of reaction, since it is a microchip having a microchannel structure, not a microplate typically used in ELISA or the like. Moreover, in the microplate proposed in Japanese Patent Laid-Open No. 9-101302, it is not possible to sufficiently improve the efficiency of reaction and the sensitivity of measurement, although it is possible to increase the surface area of the reaction surface to some extent to improve the efficiency of reaction and the sensitivity of measurement.

SUMMARY OF THE INVENTION

It is therefore an object of the present invention to eliminate the aforementioned problems and to provide a fluid handling apparatus which is capable of improving the efficiency of reaction and the sensitivity of measurement with a simple structure and of shortening a reaction time and a measuring time, when the apparatus is used as a sample analyzing apparatus for measuring a large number of specimens, and a fluid handling unit for use therein. It is another object of the present invention to allow the interior of the above described fluid handling apparatus or fluid handling unit for use therein to be efficiently washed to further improve the accuracy of analysis.

In order to accomplish the aforementioned and other objects, according to one aspect of the present invention, a fluid handling apparatus comprises an apparatus body and a plurality of fluid handling subassemblies arranged on the apparatus body, each of the fluid handling subassemblies comprising: an injecting section for injecting a fluid; a fluidized section for receiving the fluid from the injecting section to allow the fluid to continuously flow downwards; a fluid housing chamber for receiving the fluid from the fluidized section; a wall portion formed between the fluid housing chamber and the injecting section and between the fluid housing chamber and the fluidized section; an opening, formed in the wall portion, for allowing the fluid to enter the fluid housing chamber; and a surface-area increasing means, arranged in the fluidized section, for increasing an area of a contact surface with the fluid in the fluidized section, wherein the opening extends from a lower end, which is positioned in the vicinity of the lower end of the fluidized section, to an upper end, which is higher than the upper end of the fluidized section, for allowing the injecting section and the fluidized section to be communicated with the fluid housing chamber.

In this fluid handling apparatus, the opening is preferably a slit which passes through the wall portion, and the slit may have an upper portion having a width which is wider than that of a lower portion of the slit. The opening preferably has a lower end arranged at a level which is substantially equal to a bottom face of the fluid housing chamber. The apparatus body preferably comprises a frame and a plurality of supporting members which are arranged on the frame so as to be substantially parallel to each other, each of the supporting members having a plurality of recessed portions which are arranged at regular intervals in a row, and each of the plurality of fluid handling subassemblies being mounted in a corresponding one of the recessed portions.

In the above described fluid handling apparatus, the fluidized section is preferably arranged so as to surround the fluid housing chamber. Each of the plurality of recessed portions may comprise an upper recessed portion, and a lower recessed portion which is formed in a bottom face of the upper recessed portion, the fluidized section being formed between a partition wall member, which is inserted into each of the plurality of recessed portions, and the upper recessed portion, and the fluid housing chamber being surrounded by the partition wall member. In this case, an extended recessed portion for extending the upper cylindrical recessed portion in substantially horizontal directions is preferably formed in each of the plurality of recessed portions. The surface-area increasing means preferably comprises a large number of fine particles filled in the fluidized section, and may be a porous material. Moreover, a liquid injected into the injecting section preferably flows in the fluidized section and the opening due to capillarity.

According to another aspect of the present invention, a fluid handling unit comprises a supporting member and a plurality of fluid handling subassemblies which are arranged on the supporting member at regular intervals in a row, each of the fluid handling subassemblies comprising: an injecting section for injecting a fluid; a fluidized section for receiving the fluid from the injecting section to allow the fluid to continuously flow downwards; a fluid housing chamber, formed so as to be surrounded by the fluidized section, for receiving the fluid from the fluidized section; a wall portion formed between the fluid housing chamber and the injecting section and between the fluid housing chamber and the fluidized section; an opening, formed in the wall portion, for allowing the fluid to enter the fluid housing chamber; and a surface-area increasing means, arranged in the fluidized section, for increasing an area of a contact surface with the fluid in the fluidized section, wherein the opening extends from a lower end, which is positioned in the vicinity of the lower end of the fluidized section, to an upper end, which is higher than the upper end of the fluidized section, for allowing the injecting section and the fluidized section to be communicated with the fluid housing chamber.

In this fluid handling unit, the opening is preferably a slit which passes through the wall portion, and the slit may have an upper portion having a width which is wider than that of a lower portion of the slit. The opening preferably has a lower end arranged at a level which is substantially equal to a bottom face of the fluid housing chamber. The surface-area increasing means preferably comprises a large number of fine particles filled in the fluidized section, and may be a porous material. Moreover, a liquid injected into the injecting section preferably flows in the fluidized section and the opening due to capillarity.

Furthermore, throughout the specification, the term "opening" means a portion, a part of which passes through a wall portion, and includes an elongated through hole, such as a slit, which passes through a wall portion, as well as an elongated groove (recessed portion) having a through hole in a part thereof.

According to the present invention, it is possible to provide a fluid handling apparatus which is capable of improving the efficiency of reaction and the sensitivity of measurement with a simple structure and of shortening a reaction time and a measuring time, when the apparatus is used as a sample analyzing apparatus for measuring a large number of specimens, and a fluid handling unit for use therein.

BRIEF DESCRIPTION OF THE DRAWINGS

The present invention will be understood more fully from the detailed description given herebelow and from the accompanying drawings of the preferred embodiments of the invention. However, the drawings are not intended to imply limitation of the invention to a specific embodiment, but are for explanation and understanding only.

In the drawings.

DESCRIPTION OF THE PREFERRED EMBODIMENTS

Referring now to the accompanying drawings, the preferred embodiments of a fluid handling apparatus and a fluid handling unit for use therein according to the present invention will be described below in detail.

Figure 1:
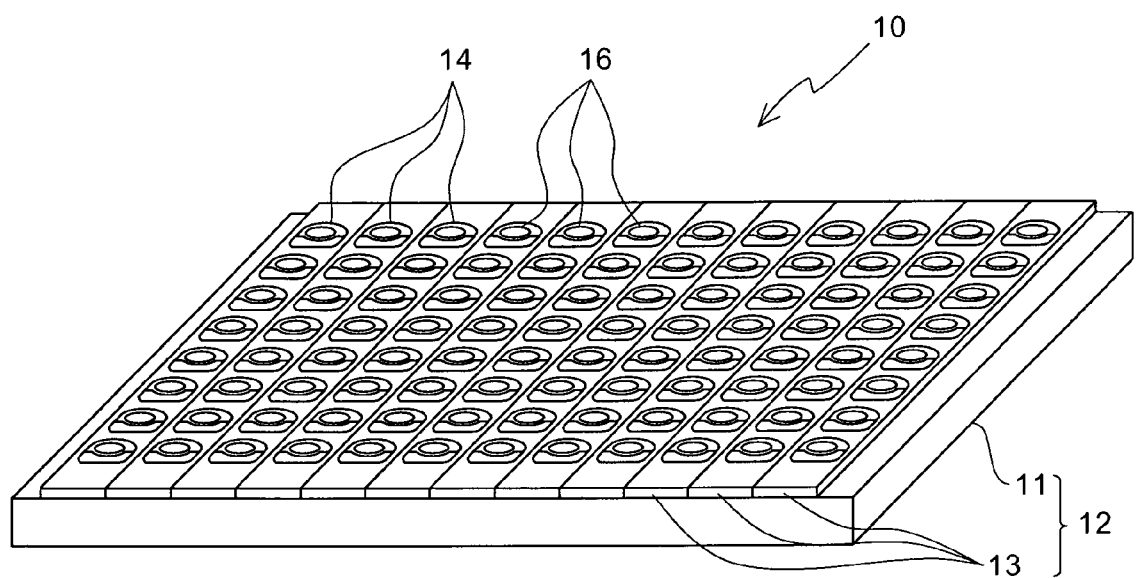
FIG. 1 is a perspective view of the first preferred embodiment of a fluid handling apparatus according to the present invention.

FIGS. 1 through 14 show the first preferred embodiment of a fluid handling apparatus according to the present invention. For example, the fluid handling apparatus 10 in this preferred embodiment can be used as an apparatus for analyzing a sample containing a biosubstance, such as a protein, which is representative of functional substances. In general, the fluid handling apparatus 10 can be used as a sample analyzing apparatus called a microwell plate for carrying out the measurement of a large number of specimens. As shown in FIG. 1, the fluid handling apparatus 10 comprises: an apparatus body 12; and a plurality of fluid handling subassemblies 16 (96(=8×12) fluid handling subassemblies in this preferred embodiment) mounted on the apparatus body 12.

Figure 2:
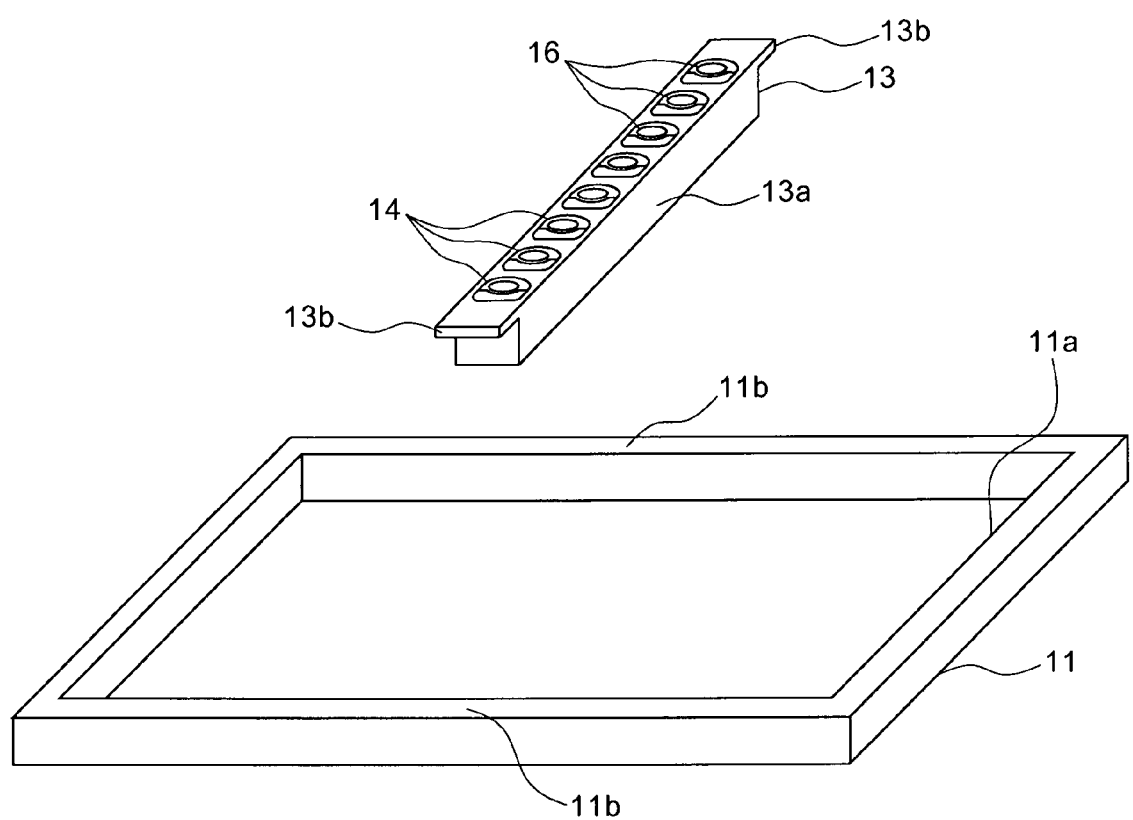
FIG. 2 is a perspective view showing a frame and a fluid handling subassemblies supporting member of the apparatus body of the fluid handling apparatus of FIG. 1.

As shown in FIGS. 1 and 2, the apparatus body 12 is made of a resin material, such as polystyrene (PS), polycarbonate (PC) or polymethyl methacrylate (PMMA), or a glass material, and comprises: a substantially rectangular frame 11 which has a substantially rectangular through hole 11a in the center thereof and which has a thickness of a few millimeters, the length of each side of the frame 11 being in the range of from a few centimeters to over ten centimeters; and a plurality of fluid handling subassemblies supporting members 13 (12 fluid handling subassemblies supporting members in this preferred embodiment) mounted on the frame 11. Furthermore, the through hole 11a of the frame 11 may be replaced with a recessed portion with bottom. Alternatively, the frame 11 may be a standard frame, such as a frame for microplate of SBS (Society for Biomolecular Screening) standard. The fluid handling subassemblies supporting members 13 may be made of a transparent material. However, if the fluid handling apparatus 10 in this preferred embodiment is used for measuring fluorescence, the fluid handling subassemblies supporting members 13 is preferably made of a member (e.g., a black member) which is difficult to allow light to pass through the member in order to suppress the rise of background during the measurement of fluorescence.

As shown in FIG. 2, each of the fluid handling subassemblies supporting members 13 comprises: an elongated supporting member body 13a having a shape of substantially rectangular parallelepiped, the length of which is substantially equal to the width of the through hole 11a of the frame 11; and a pair of substantially rectangular protruding portions 13b which protrude from the upper portions of the supporting member body 13a at both ends in longitudinal directions to extend along the upper surface of the supporting member body 13a. As shown in FIG. 1, the supporting member bodies 13a of the fluid handling subassemblies supporting members 13 are inserted into the through hole 11a of the frame 11 to be mounted on the frame 11 substantially in parallel and adjacent to each other so that the protruding portions 13b are supported on a pair of upper surfaces 11b of the frame 11 extending in longitudinal directions. Thus, the apparatus body 12 is assembled.

Figure 3:
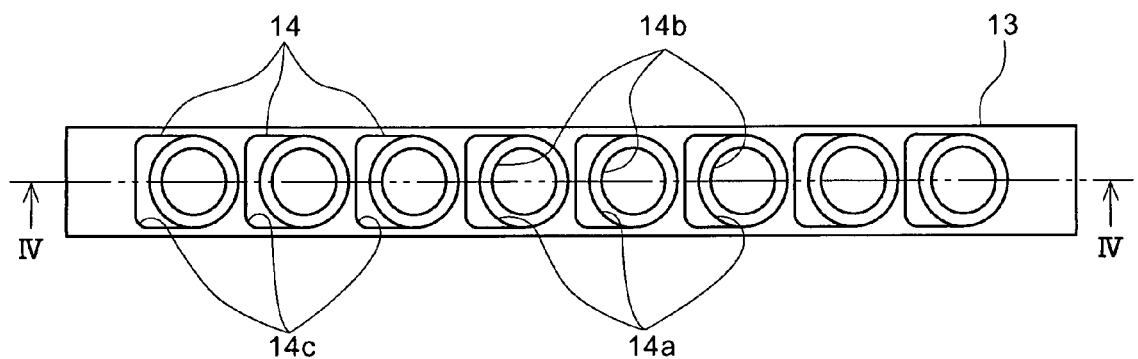
FIG. 3 is an enlarged plan view of the fluid handling subassemblies supporting member of FIG. 2.
Figure 4:
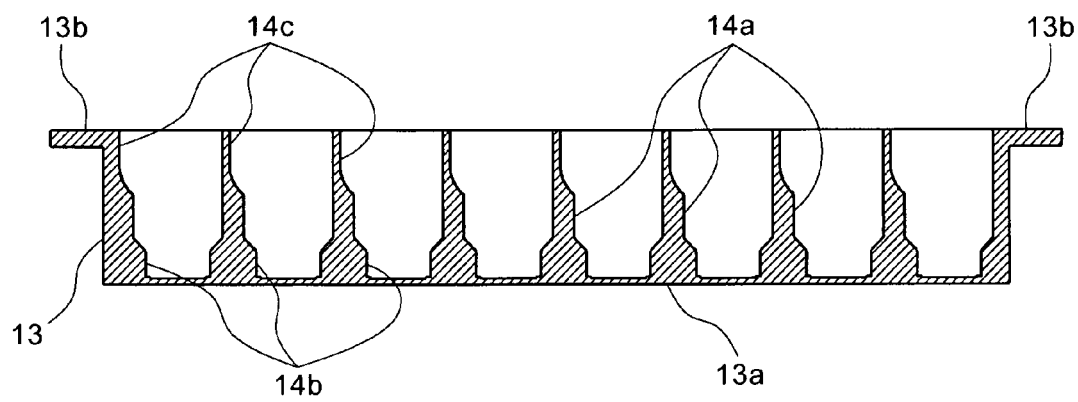
FIG. 4 is a sectional view taken along line IV-IV of FIG. 3.
Figure 5:
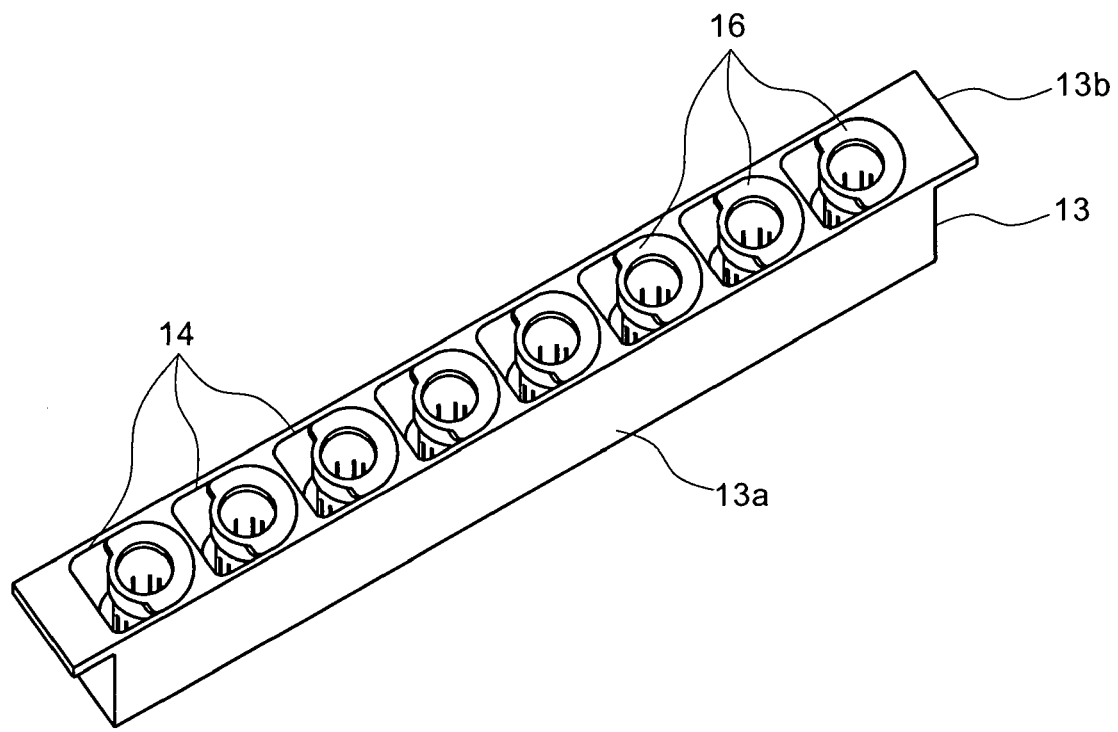
FIG. 5 is a perspective view showing a state that fluid handling subassemblies are mounted on the fluid handling subassemblies supporting member of FIG. 2.

As shown in FIGS. 3 and 4, a plurality of recessed portions 14 (eighth recessed portions 14 in this preferred embodiment) (which will be hereinafter referred to as "mounting recessed portions 14") are formed in the upper surface of the supporting member body 13a of each of the fluid handling subassemblies supporting members 13 so as to be arranged at regular intervals in a row. In each of the mounting recessed portions 14, one of the fluid handling subassemblies 16 is mounted as shown in FIG. 5. As shown in FIGS. 3 and 4, each of the mounting recessed portions 14 comprises: a substantially cylindrical large-diameter recessed portion 14a formed in the upper surface of the supporting member body 13a; an extended recessed portion 14c which is adjacent to the large-diameter recessed portion 14a to be formed in the upper surface of the supporting member body 13 so as to extend the upper portion of the large-diameter recessed portion 14a substantially in horizontal directions and which has a half depth of the large-diameter recessed portion 14a; and a substantially cylindrical small-diameter recessed portion 14b which is formed in a substantially central portion of the bottom face of the large-diameter recessed portion 14a. Two facing surfaces of the extended recessed portion 14c extending from the large-diameter recessed portion 14a extend along the side face of the supporting member body 13a of the fluid handling subassemblies supporting member 13 extending in longitudinal directions (see FIGS. 6 and 8). The bottom face of the extended recessed portion 14c is curved and inclined downwards as a distance from the large-diameter recessed portion 14a is decreased, and the bottom face of the large-diameter recessed portion 14a is inclined downwards as a distance from the small-diameter recessed portion 14b is decreased (see FIGS. 7 and 9). The bottom face of the small-diameter recessed portion 14b has a fine recessed portion 14d, which has a fine depth and a diameter substantially equal to the inside diameter of a cylindrical member 20 which will be described later, so as to form a gap for preventing the occurrence of interference fringe between the bottom face of the cylindrical member 20 and the bottom face of the mounting recessed portion 14 when the cylindrical member 20 is fitted into the small-diameter recessed portion 14b.

Figure 6:
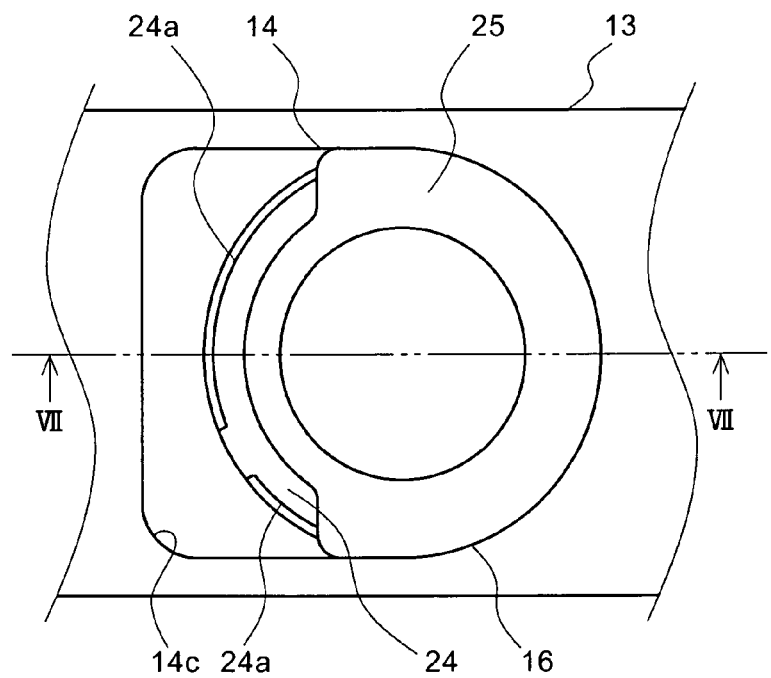
FIG. 6 is an enlarged plan view of one of the fluid handling subassemblies of the fluid handling apparatus of FIG. 1.
Figure 7:
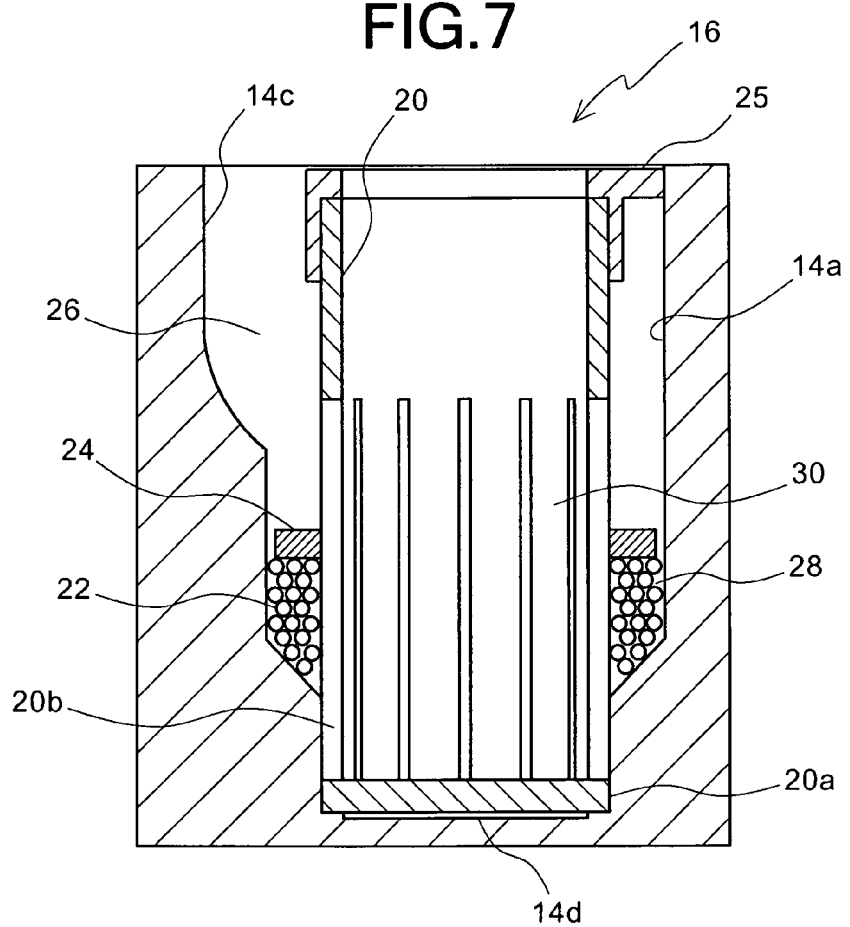
FIG. 7 is a sectional view taken along line VII-VII of FIG. 6.
Figure 8:
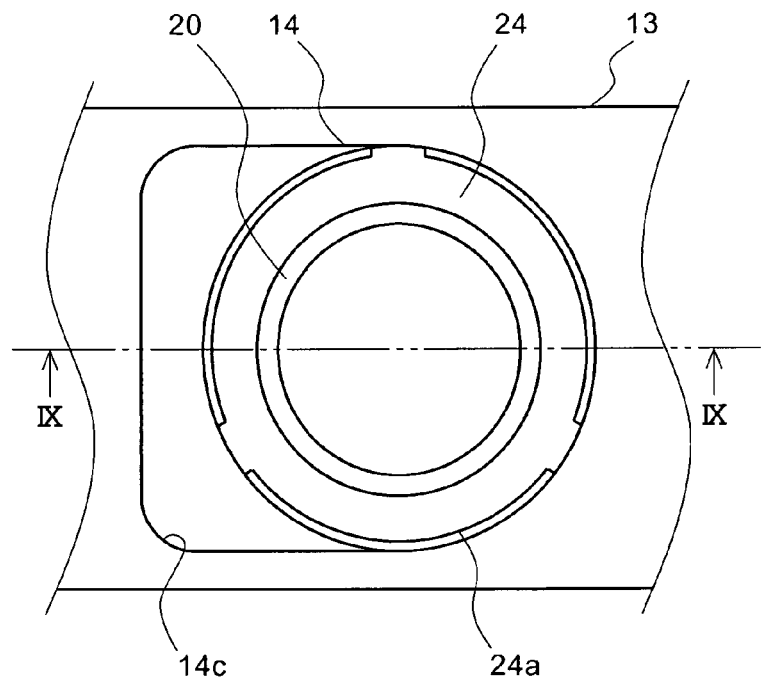
FIG. 8 is a plan view showing a state that a lid member is removed from the fluid handling apparatus of FIG. 6.
Figure 9:
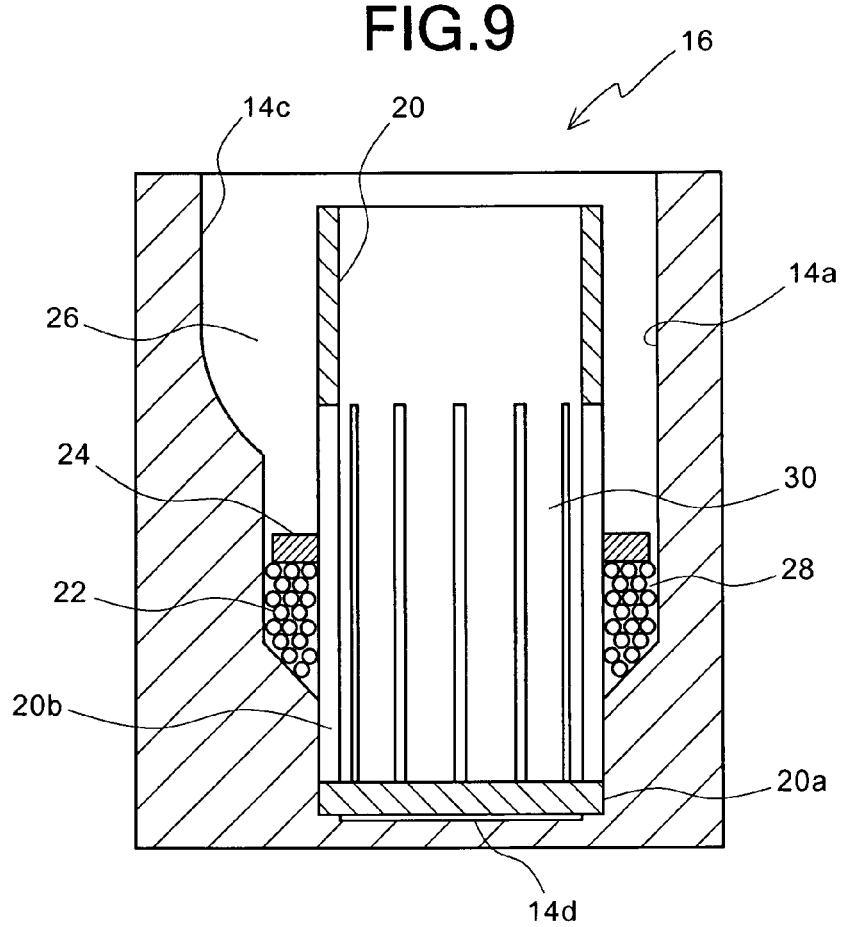
FIG. 9 is a sectional view taken along line IX-IX of FIG. 8.
Figure 10:
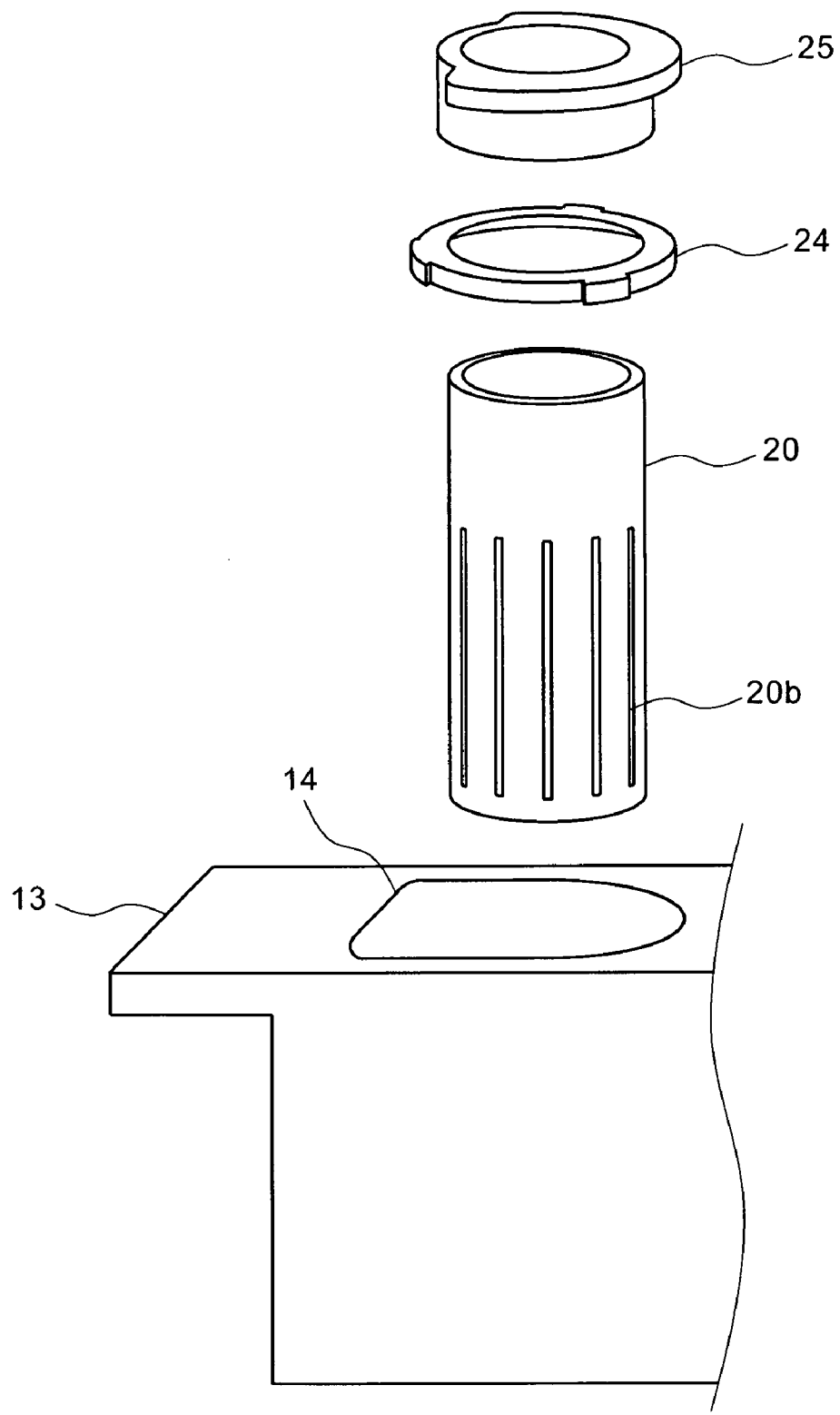
FIG. 10 is an exploded perspective view showing one of the fluid handling subassemblies of the fluid handing apparatus of FIG. 1, except for beads.
Figure 11:
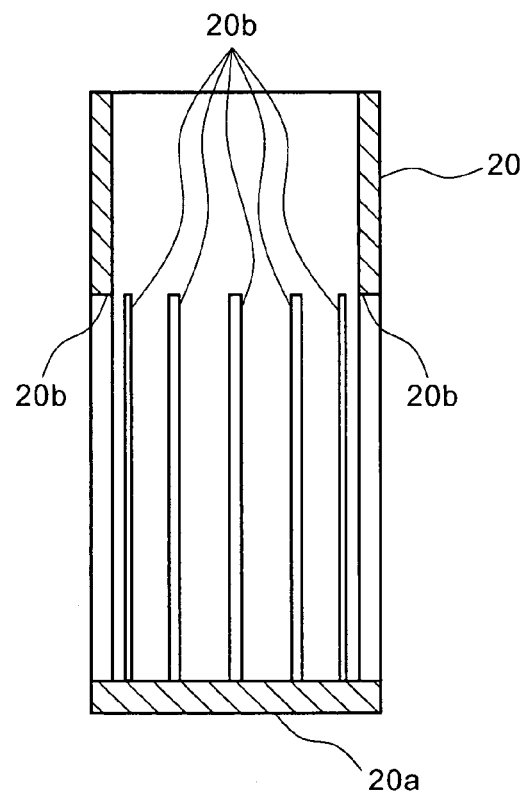
FIG. 11 is a sectional view of a cylindrical member of one of the fluid handling subassemblies of the fluid handling apparatus of FIG. 1.
Figure 12:
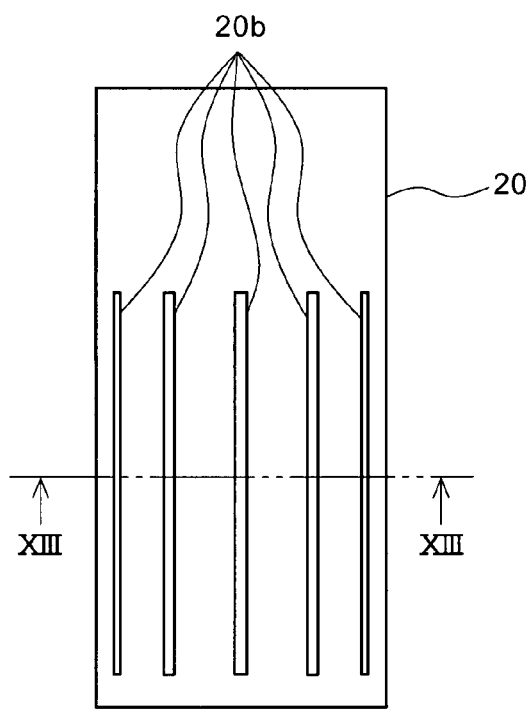
FIG. 12 is a side view of the cylindrical member of FIG. 11.
Figure 13:
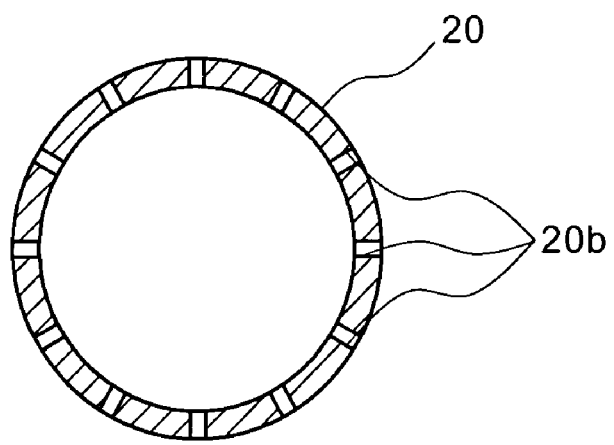
FIG. 13 is a sectional view taken along line XIII-XIII of FIG. 12.
Figure 14:
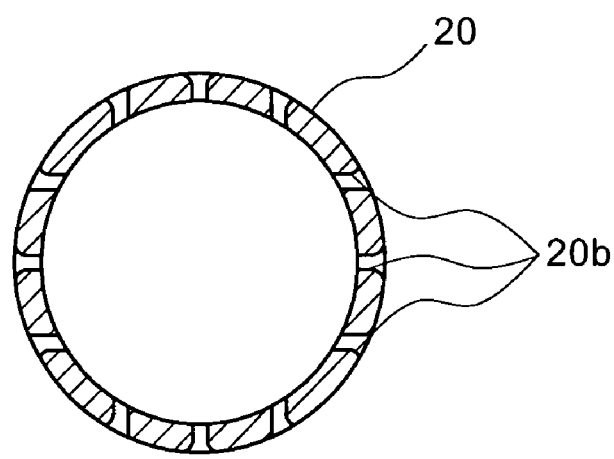
FIG. 14 is a sectional view showing a modified example of the cylindrical member of FIG. 11.

FIGS. 6 through 10 are enlarged views showing one of the fluid handling subassemblies 16, each of which is mounted in a corresponding one of the mounting recessed portions 14 of the fluid handling apparatus 10 in this preferred embodiment. FIG. 6 is a plan view of one of the fluid handling subassemblies 16, each of which is mounted in a corresponding one of the mounting recessed portions 14 of the fluid handling apparatus 10, and FIG. 7 is a sectional view taken along line VII-VII of FIG. 6. FIG. 8 is a plan view showing a state that a lid member 25 is removed from one of the fluid handling subassemblies 16 of FIG. 6, and FIG. 9 is a sectional view taken along line IX-IX of FIG. 8. FIG. 10 is an exploded perspective view of one of the fluid handling subassemblies 16 (except for beads 22). FIG. 11 is a sectional view of a cylindrical member 20 of the fluid handling subassembly 16 of FIG. 7, and FIG. 12 is a side view of the cylindrical member 20 of FIG. 11. FIG. 13 is a sectional view taken along line XIII-XIII of FIG. 12, and FIG. 14 is a sectional view showing a modified example of the cylindrical member 20 of FIG. 11.

As shown in FIGS. 6 through 10, each of the fluid handling subassemblies 16 comprises: a cylindrical member 20 having a substantially cylindrical shape which has a diameter and height of a few millimeters; a large number of substantially spherical fine beads 22; a substantially annular disk-shaped partition plate 24; and a lid member 25.

As shown in FIGS. 7 and 9, the cylindrical member 20 has a length which is substantially equal to the depth of the mounting recessed portion 14 (the depth of the large-diameter recessed portion 14a and small-diameter recessed portion 14b), and an outside diameter which is substantially equal to the inside diameter of the small-diameter recessed portion 14b of the mounting recessed portion 14. The bottom portion of the cylindrical member 20 is designed to be fitted into the small-diameter recessed portion 14b of the mounting recessed portion 14. Furthermore, since the extended recessed portion 14c is formed in this preferred embodiment, even if the inside diameter of the small-diameter recessed portion 14b and the outside diameter of the cylindrical member 20 are increased to decrease a gap between the cylindrical member 20 and the large-diameter recessed portion 14a, it is possible to ensure a sufficiently large inlet of an injecting section 26 which will be described later. For example, the inside diameter of the cylindrical member 20 may be about 4.5 mm. The cylindrical member 20 has a bottom portion 20a. As shown in FIGS. 11 and 12, the outer periphery of the cylindrical member 20 has one or a plurality of slits 20b (twelve slits 20b in this preferred embodiment) which allow liquid to pass therethrough and which inhibit the beads 22 from passing therethrough. The slits 20b pass through the cylindrical member 20 so as to extend from the upper face of the bottom portion 20a in longitudinal directions in parallel. The length of each of the slits 20b is greater than half of the length of the cylindrical member 20, and the upper end of each of the slits 20b is arranged above the partition plate 24 when the fluid handling subassembly 16 is mounted in the mounting recessed portion 14. Furthermore, the slits 20b are radially formed in the outer periphery of the cylindrical member 20 as shown in FIG. 13 in this preferred embodiment. However, the slits 20b may be formed so as to pass through the outer periphery of the cylindrical member 20 while extending in four directions as shown in FIG. 14 in order to facilitate the molding of the cylindrical member 20.

The central portion of the partition plate 24 has a substantially circular opening into which the cylindrical member 20 is fitted. The peripheral portion of the partition plate 24 has a plurality of cut-out portions 24a (three cut-out portions 24a in this preferred embodiment) which extend in circumferential directions at regular intervals. The outside diameter of the partition plate 24 is substantially equal to the inside diameter of the large-diameter recessed portion 14a of the mounting recessed portion 14, so that the partition plate 24 is fitted into the large-diameter recessed portion 14a of the mounting recessed portion 14 when it is inserted into the mounting recessed portion 14.

The lid member 25 comprises: a cylindrical fitted portion which has an inside diameter substantially equal to the outside diameter of the cylindrical member 20 and which can be fitted into the opening of the upper end portion of the cylindrical member 20; and a flange portion which extends outwards in radial directions from a part of the upper end portion of the fitted portion. The flange portion extends so as to close the upper end portion of a space between the large-diameter recessed portion 14a of the mounting recessed portion 14 and the cylindrical member 20, except for a portion on the side of the extended recessed portion 14c of the mounting recessed portion 14.

In order to assemble the fluid handling subassembly 16 with this construction, the lower portion of the cylindrical member 20 is first fitted into the small-diameter recessed portion 14b of the mounting recessed portion 14 to be fixed thereto with an adhesive or the like. Then, a large number of beads 22 are filled in an annular space between the large-diameter recessed portion 14a of the mounting recessed portion 14 and the cylindrical member 20. Then, the cylindrical member 20 is fitted into the opening of the partition plate 24 which is arranged on the beads 22 to be fixed thereto with an adhesive or the like. Thereafter, the lid member 25 is fitted into the opening of the upper end portion of the cylindrical member 20.

If the fluid handling subassembly 16 is thus mounted in the mounting recessed portion 14, a space serving as an injecting section 26 for injecting a fluid, such as a liquid sample, is formed between the cylindrical member 20 and the large-diameter recessed portion 14a and extended recessed portion 14c of the mounting recessed portion 14 over the partition plate 24. A portion of the upper end portion of the injecting section 26, which is not closed by the lid member 25 and which is arranged on the side of the extended recessed portion 14c, serves as an inlet. Below the injecting section 26, a fluidized section 28, which is a substantially annular space capable of being used as a reaction section filled with the large number of beads 22, is formed between the large-diameter recessed portion 14a of the mounting recessed portion 14 and the cylindrical member 20. The fluidized section 28 is communicated with the injecting section 26 via the cut-out portions 24a of the partition plate 24 serving as fluidized section inlets. In the cylindrical member 20, there is formed a fluid housing chamber 30 which is a substantially cylindrical space capable of being used as a measuring section. The fluid housing chamber 30 thus formed is communicated with the injecting section 26 and fluidized section 28 via the slits 20b.

Thus, in the fluid handling subassembly 16 in this preferred embodiment, the interior of the mounting recessed portion 14 having a size, which is equal to that of each of wells of a microplate, is divided into the fluidized section 28, which can be used as a reaction section, and the fluid housing chamber 30, which can be used as a measuring section, by the cylindrical member 20 extending in substantially vertical directions. Thus, even if the quantity of a liquid, such as a reagent injected from an inlet, is small, the liquid can sequentially flow in the fluidized section 28 due to capillarity or the like without the need of any external powers. If the fluid housing chamber 30 formed in the cylindrical member 20 is used as a measuring section, a liquid can be fed from the fluidized section 28 into the liquid housing chamber 30, which has a smaller diameter than that of the large-diameter recessed portion 14a of the mounting recessed portion 14 which has a diameter equal to each of wells of a microplate, to raise the liquid level, so that the quantity of a reagent to be used can be decreased to reduce costs.

Referring to FIGS. 21A through 21I, 22A through 22F, and 23A through 23F, when the injection of a liquid sample into the fluid handling apparatus 10 in this preferred embodiment and the washing of the interior thereof are carried out, the flow of liquid will be described below.

Figure 21A:
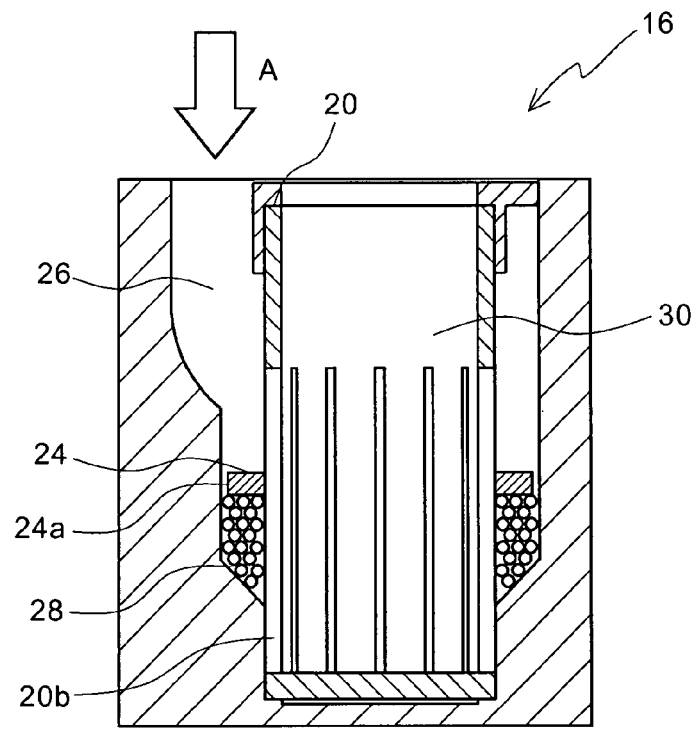
FIGS. 21A through 21I are illustrations for explaining the flow of a liquid sample when the liquid sample is injected into one of the fluid handling subassemblies of the fluid handling apparatus of FIG. 1.
Figure 21B:
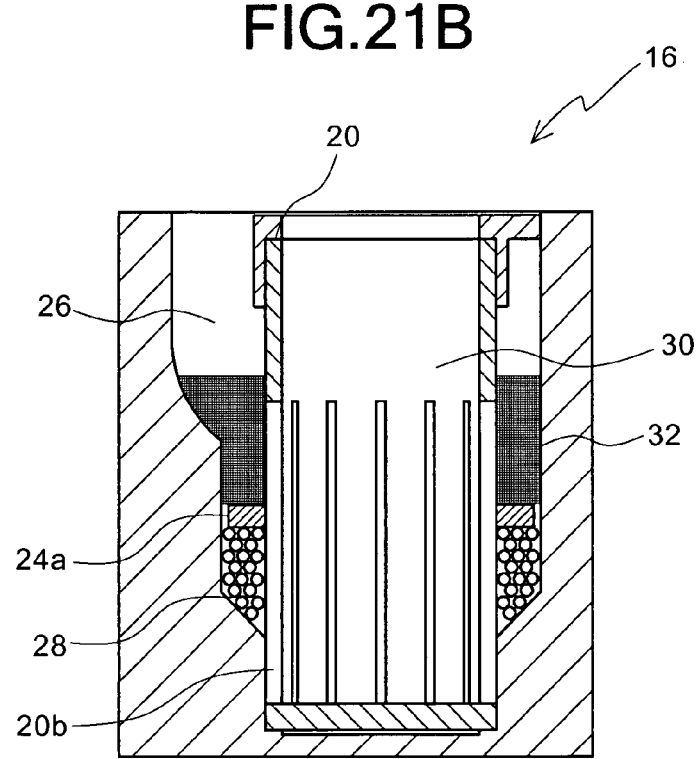
Figure 21C:
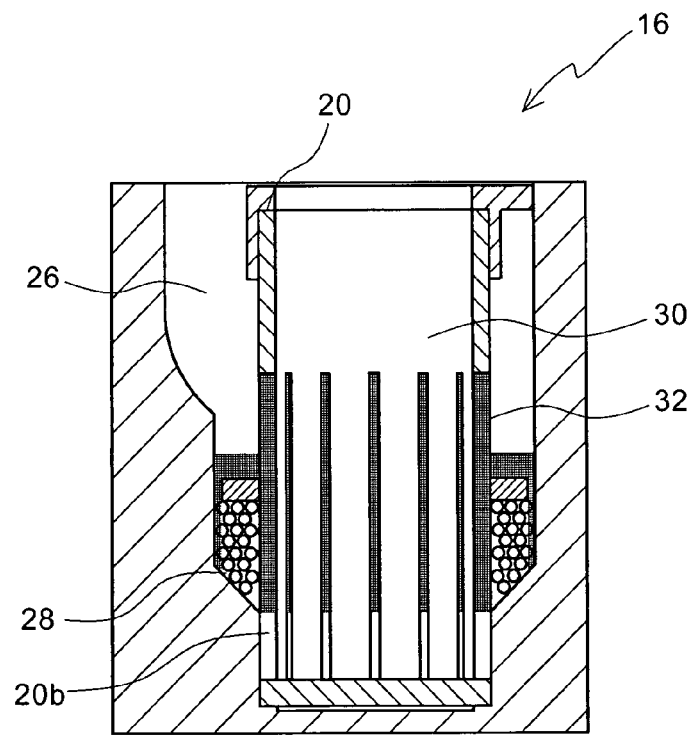
Figure 21D:
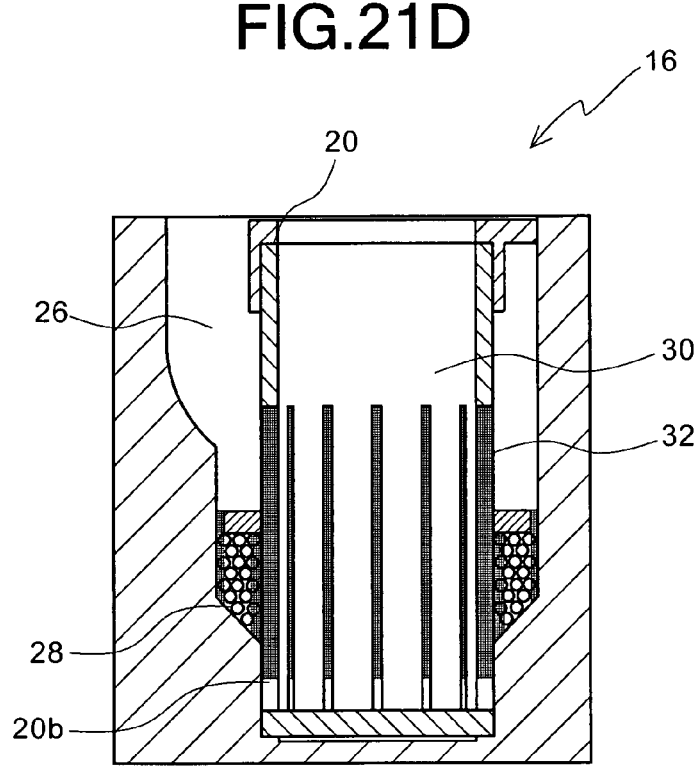
Figure 21E:
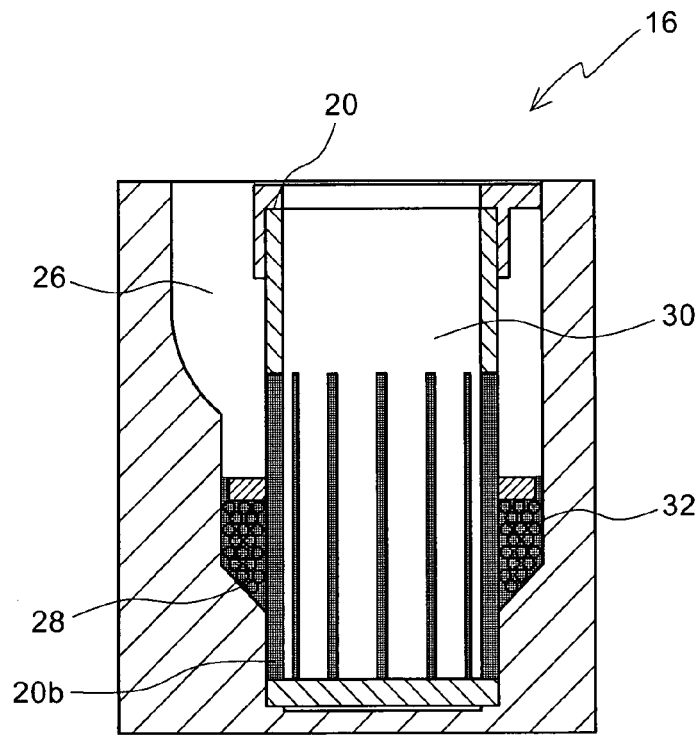
Figure 21F:
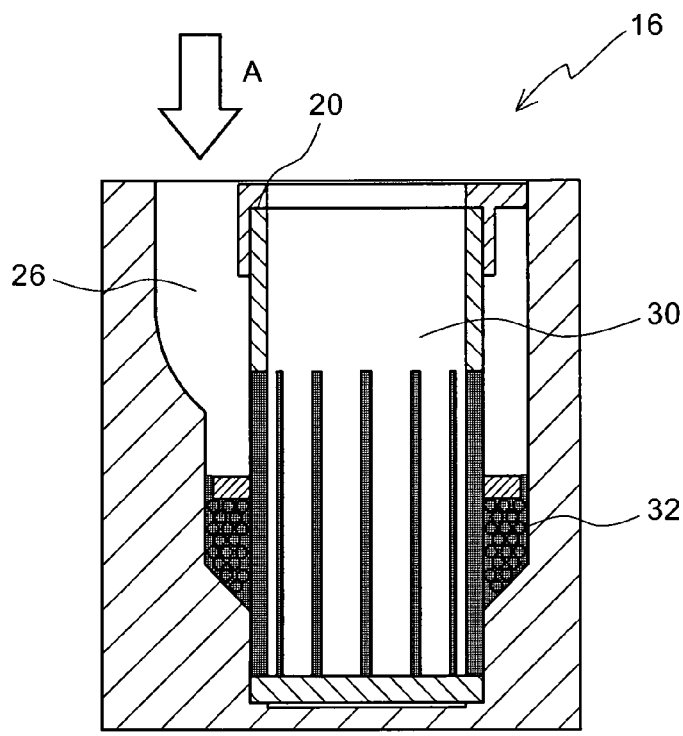
Figure 21G:
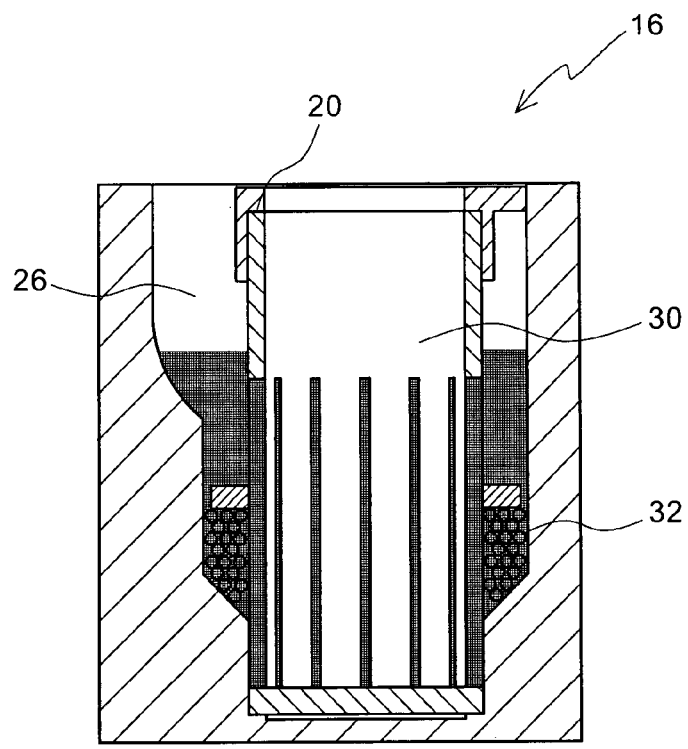
Figure 21H:
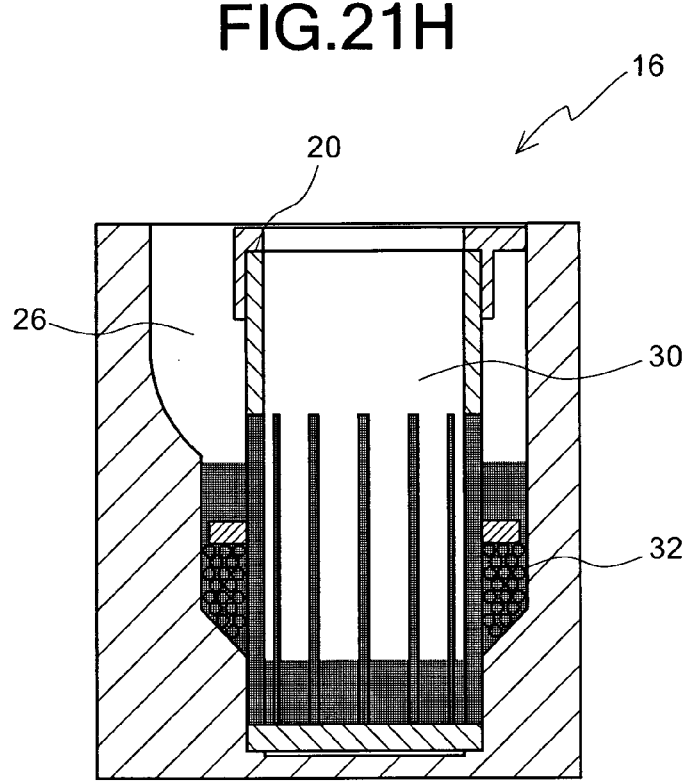
Figure 21I:
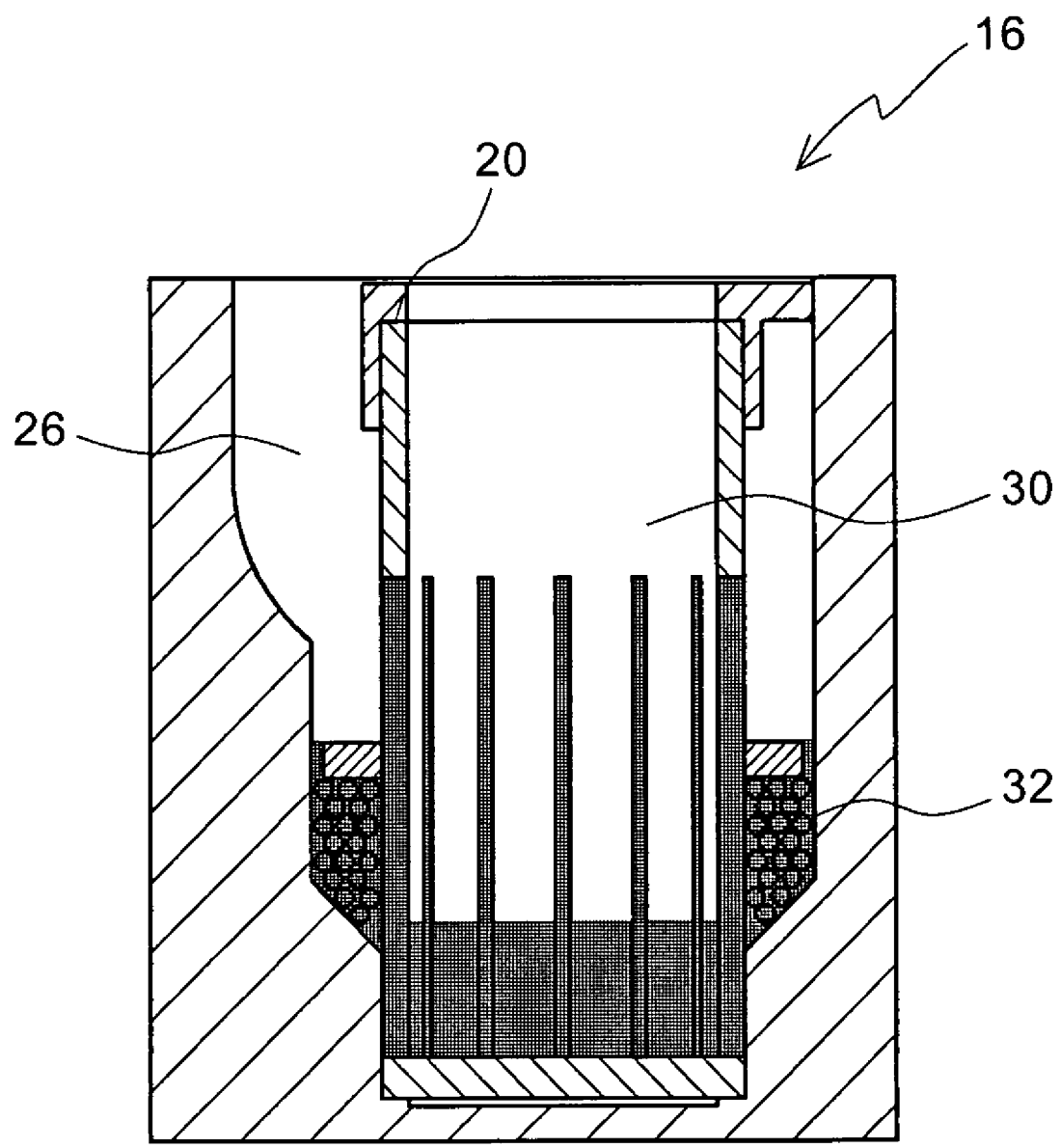

First, if a liquid sample 32 is gradually injected from the inlet of the injecting section 26 of the fluid handling subassembly 16 as shown by arrow A in FIG. 21A, the injected liquid sample 32 is fed into the injecting section 26 as shown in FIG. 21B. Then, as shown in FIG. 21C, the liquid sample 32 is fed into the fluidized section 28 via the fluidized section inlets (the cut-out portions 24a of the partition plate 24), and is fed directly into the slits 20b of the cylindrical member 20. Thereafter, as shown in FIGS. 21D and 21E, the liquid sample 32 fed into the fluidized section 28 from the fluidized section inlets, and the liquid sample 32 fed into the slits 20b are extended so as to be filled in the whole fluidized section 28, and are extended in the whole slits 20b due to capillarity. Until this state, the liquid sample 32 is not fed into the fluid housing chamber 32 by the surface tension of the liquid sample 32 in the slits 20b. Thereafter, if the liquid sample 32 is further injected as shown by arrow A in FIG. 21F, the liquid sample 32 is fed along the bottom face of the fluid housing chamber 30 to be stored in the fluid housing chamber 30 after being fed into the injecting section 26 as shown in FIGS. 21G through 21I.

Figure 22A:
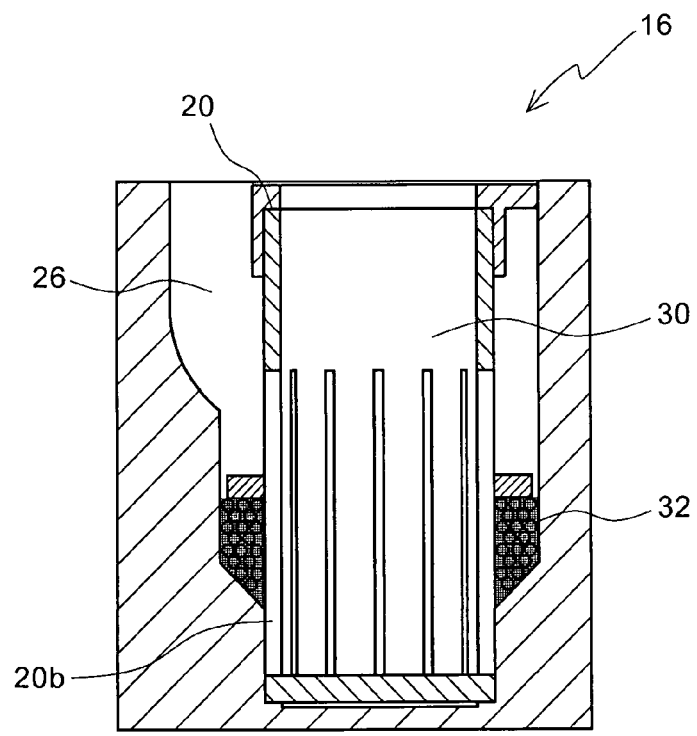
FIGS. 22A through 22F are illustrations for explaining the flow of a washing solution and the remaining liquid sample when the washing solution is injected for washing the interior of one of the fluid handling subassemblies of the fluid handling apparatus after the liquid sample is injected into and discharged from the one of the fluid handling subassemblies as shown in FIGS. 21A through 21I.
Figure 22B:
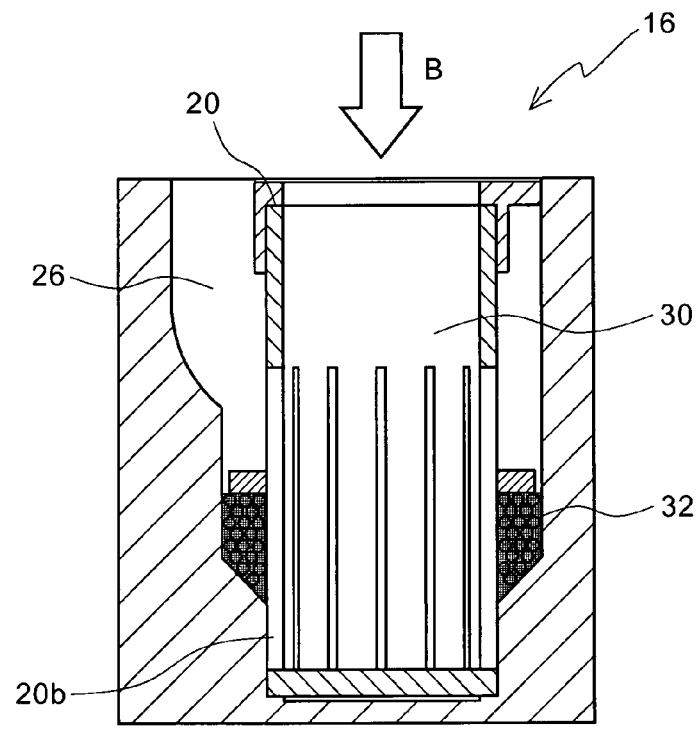
Figure 22C:
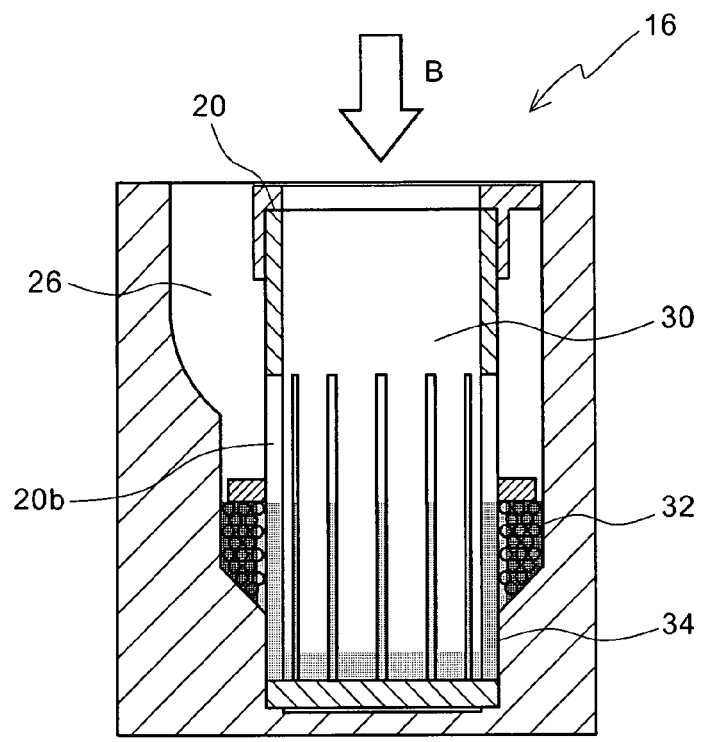
Figure 22D:
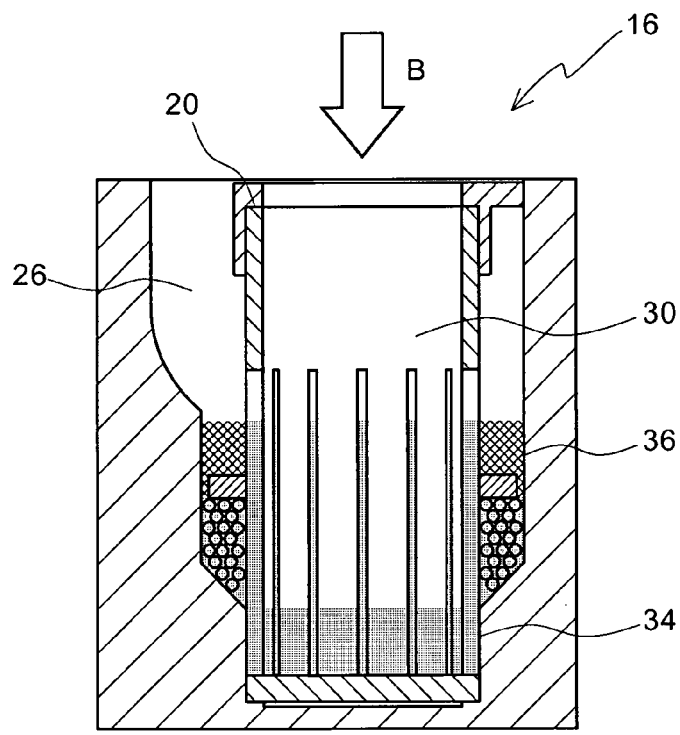
Figure 22E:
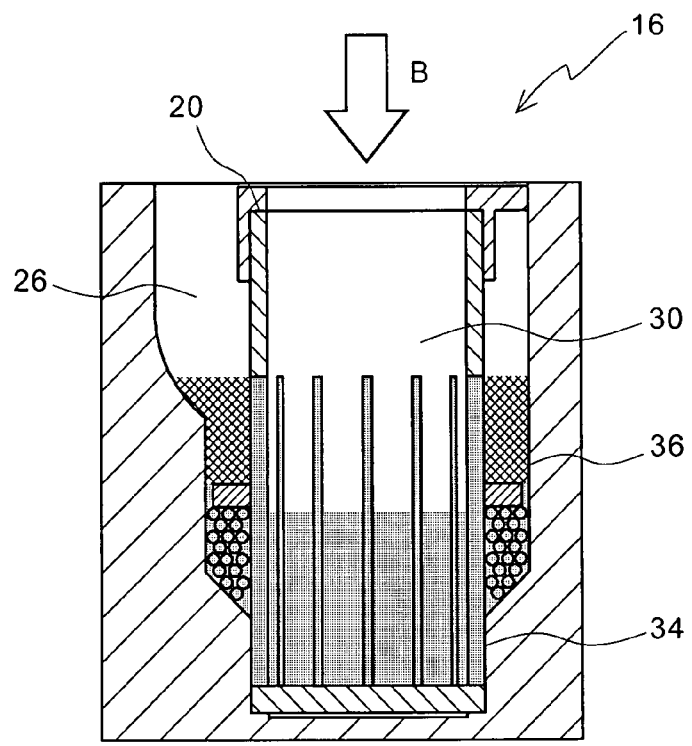
Figure 22F:
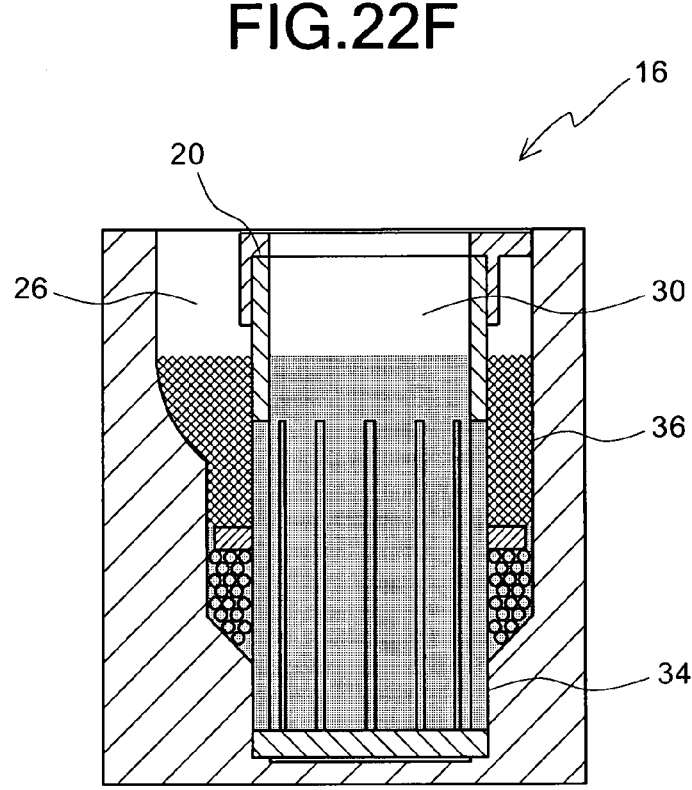

Then, even if the liquid sample 32 is discharged from the fluid handling subassembly 16, part of the liquid sample 32 adheres to the beads 22 in the fluidized section 28 to remain in the fluidized section 28 as shown in FIG. 22A. In this state, if a washing solution 34 is injected from the opening of the fluid housing chamber 30 as shown by arrow B in FIGS. 22B through 22E, the injected washing solution 34 is first fed from the bottom portion of the fluid housing chamber 30 into the slits 20b of the cylindrical member 20 as shown in FIG. 22C. Then, the washing solution 34 is extended in the slits 20b, and is fed into the fluidized section 28. Thereafter, if the washing solution 34 is further injected, the liquid sample 32 remaining in the fluidized section 28 is diluted with the washing solution 34 to be pushed up as a mixed solution 36 of the liquid sample 32 and washing solution 34, which is fed into the injecting section 26 above the fluidized section 28, as shown in FIGS. 22D through 22F.

Figure 23A:
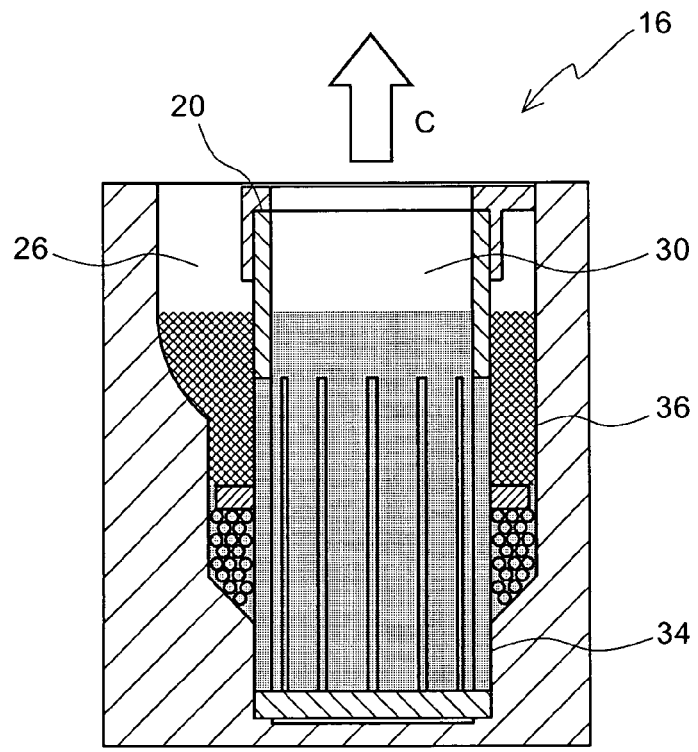
FIGS. 23A through 23F are illustrations for explaining the flow of the washing solution and the remaining liquid sample when the washing solution is sucked from the one of the fluid handling subassemblies of the fluid handling apparatus after the washing solution is injected into the one of the fluid handling subassemblies of the fluid handling apparatus as shown in FIGS. 22A through 22F.
Figure 23B:
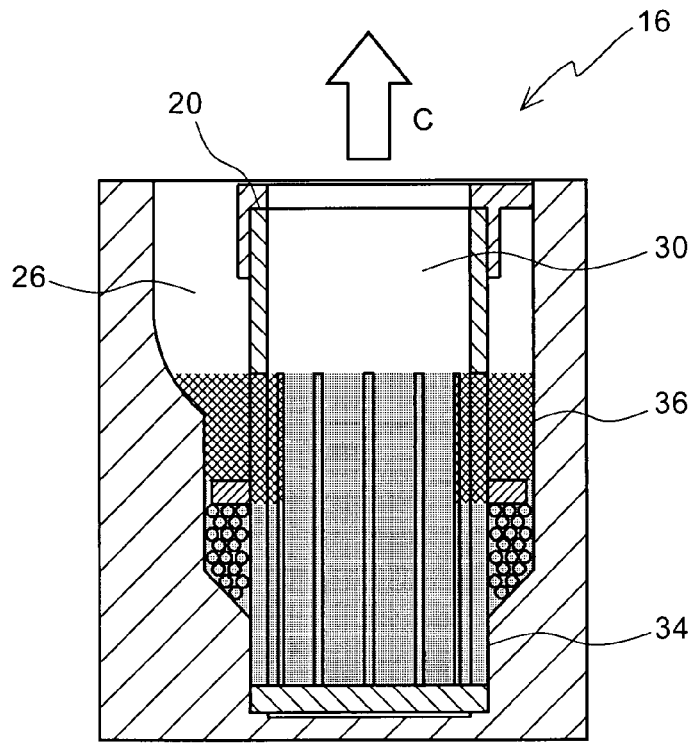
Figure 23C:
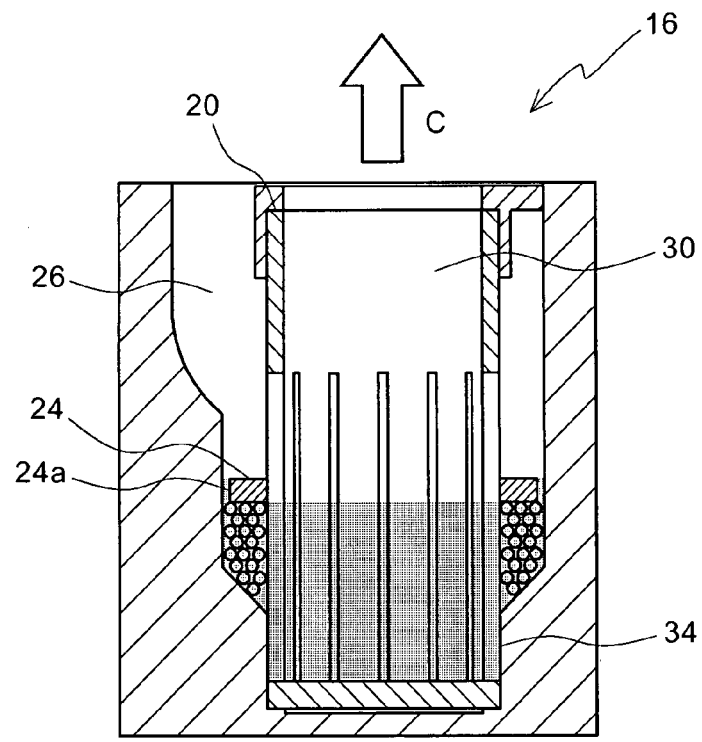
Figure 23D:
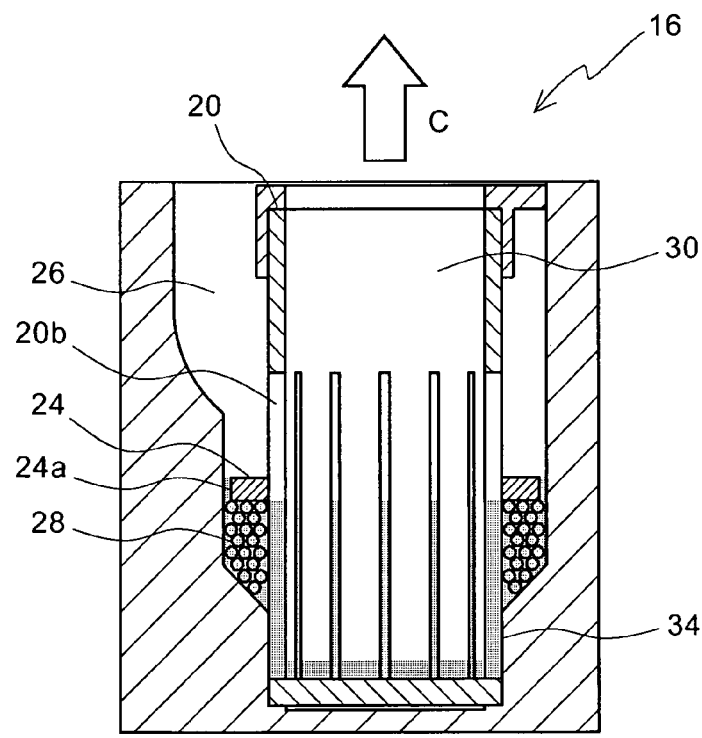
Figure 23E:
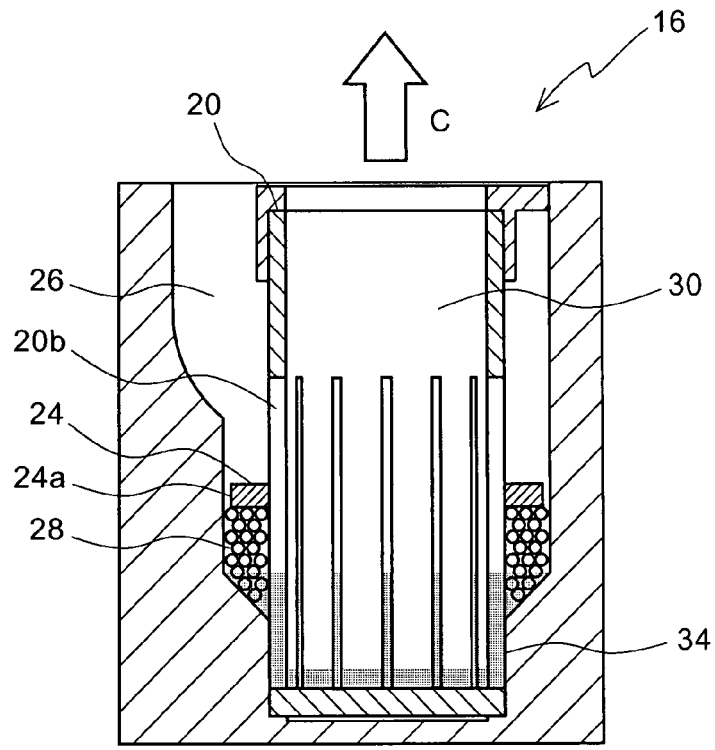
Figure 23F:
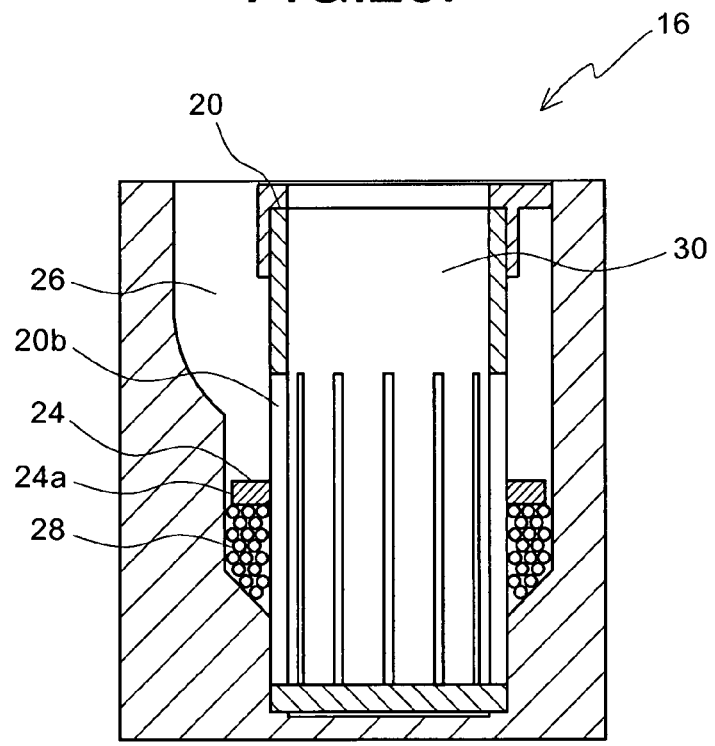

Then, a suction pipe (not shown) is inserted into the opening of the fluid housing chamber 30 so as to approach the bottom face of the fluid housing chamber 30 in order to suck the washing solution 34 as shown by arrow C in FIGS. 23A through 23E. First, as shown in FIGS. 23A through 23C, the washing solution 34 is sucked, and the most part of the mixed solution 36 fed into the injecting section 26 is fed directly into the fluid housing chamber 30 via the slits 20b of the cylindrical member 20 without passing through the fluidized section 28, so that the mixed solution 36 is further diluted with the washing solution 34. Thereafter, the washing solution 34 (the mixed solution 36 diluted with the washing solution 34) is discharged from the bottom portion of the fluid housing chamber 30, so that the interior of the fluid handling subassembly 16 is washed.

Thus, when the washing solution 34 is injected into the fluid handling subassembly 16 of the fluid handling apparatus 10 in this preferred embodiment, the most part of the mixed solution 36 of the remaining liquid sample 32 and washing solution 34 is pushed up to the injecting section 26 from the fluidized section 28 filled with the beads 22. Thereafter, when the washing solution 34 is sucked from the fluid handling subassembly 16, the most part of the mixed solution 36 is fed directly into the fluid housing chamber 30 via the slits 20b to be discharged to the outside without passing through the fluidized section 28. Therefore, it is possible to inhibit the mixed solution 36 from contacting and adhering to the beads 22 in the fluidized section 28 again when the washing solution 34 is sucked, so that it is possible to efficiently wash the interior of the fluid handling subassembly 16 to improve the accuracy of analysis.

Second Preferred Embodiment

Figure 15:
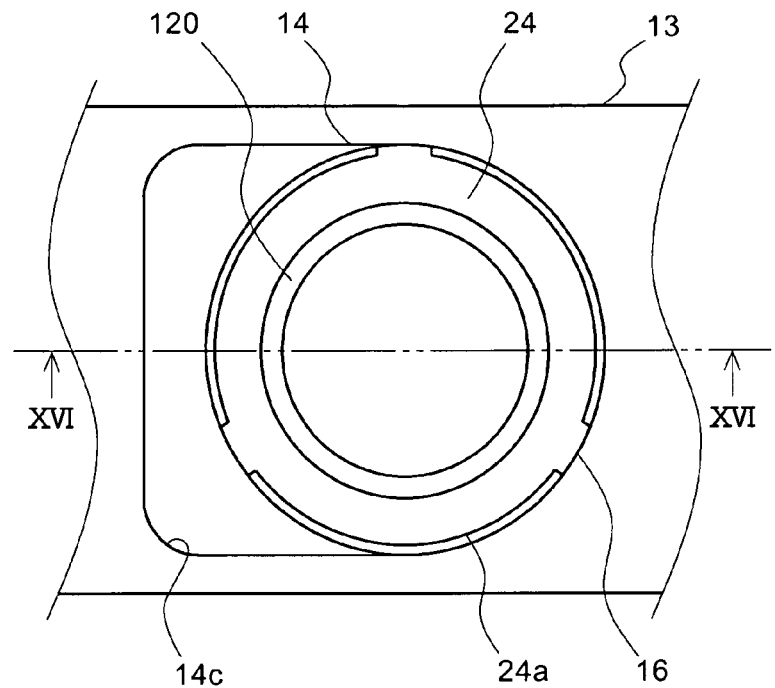
FIG. 15 is a plan view of one of fluid handling subassemblies of the second preferred embodiment of a fluid handling apparatus according to the present invention.
Figure 16:
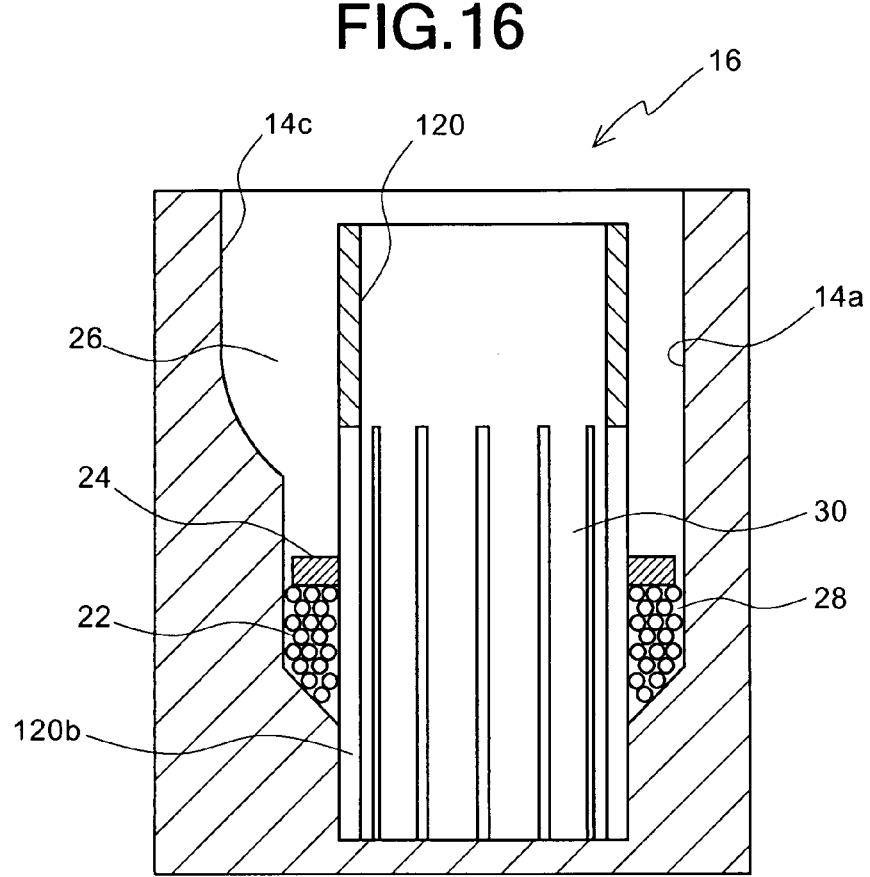
FIG. 16 is a sectional view taken along line XVI-XVI of FIG. 15.
Figure 17:
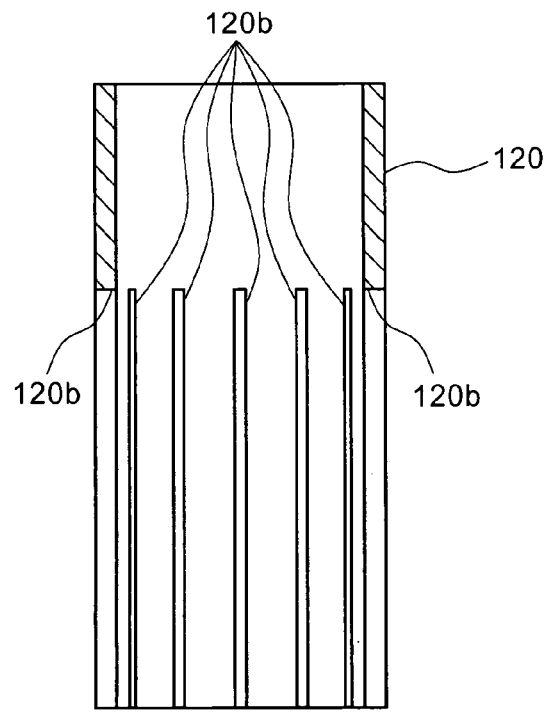
FIG. 17 is a sectional view of a cylindrical member of one of the fluid handling subassemblies of the fluid handling apparatus of FIG. 15.
Figure 18:
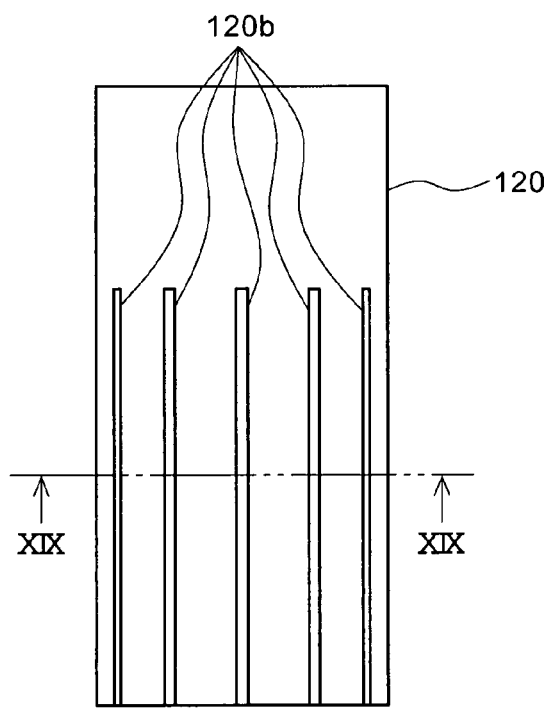
FIG. 18 is a side view of the cylindrical member of FIG. 17.
Figure 19:
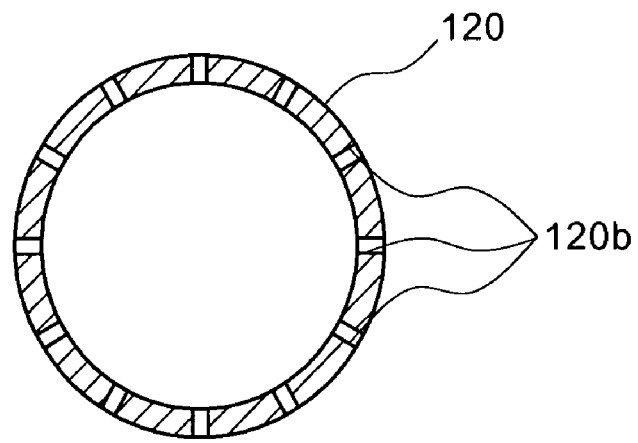
FIG. 19 is a sectional view taken along line XIX-XIX of FIG. 18.
Figure 20:
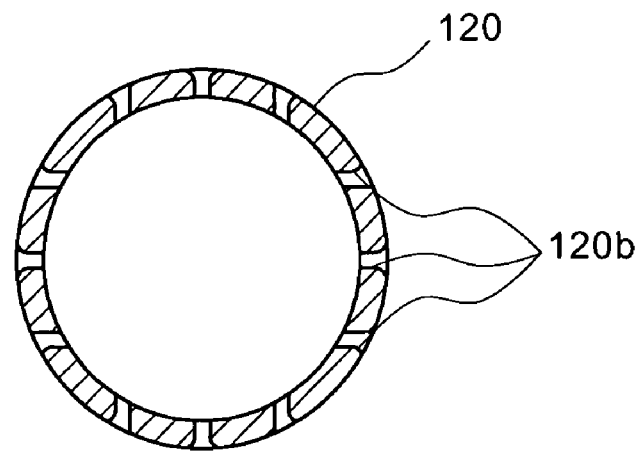
FIG. 20 is a sectional view showing a modified example of the cylindrical member of FIG. 17.

FIGS. 15 through 20 show one of fluid handling subassemblies 16 of the second preferred embodiment of a fluid handling apparatus according to the present invention. FIG. 15 is a plan view of one of fluid handling subassemblies 16 in this preferred embodiment, which is mounted in a corresponding one of mounting recessed portions 14 of a fluid handling apparatus, and FIG. 16 is a sectional view taken along line XVI-XVI of FIG. 15. FIG. 17 is a sectional view of a cylindrical member 120 of one of the fluid handling subassemblies 16 of FIG. 15, and FIG. 18 is a side view of the cylindrical member 120 of FIG. 17. FIG. 19 is a sectional view taken along line XIX-XIX of FIG. 18, and FIG. 20 is a sectional view showing a modified example of the cylindrical member 120 of FIG. 17.

In the fluid handling subassembly 16 in this preferred embodiment, the cylindrical member 120 having no bottom portion is used in place of the cylindrical member 20 with the bottom portion 20a of the fluid handling subassembly 16 in the first preferred embodiment. Therefore, no interference fringe occurs between the bottom face of the cylindrical member 120 and the bottom face of the mounting recessed portion 14, so that the fine recessed portion 14d is not formed in the bottom face of the small-diameter recessed portion 14b. In addition, slits 120b extend to the bottom end of the cylindrical member 120 since the cylindrical member 120 has no bottom portion. Moreover, the lid member 25 of the fluid handling subassembly 16 in the first preferred embodiment is not provided. Since other structural portions of the fluid handling subassembly 16 in this preferred embodiment are the same as those of the fluid handling subassembly 16 in the first preferred embodiment, the same reference numbers are given to the same structural portions as those of the fluid handling subassembly 16 in the first preferred embodiment to omit the duplicate descriptions thereof. In addition, since the flow of liquid is the same as that in the first preferred embodiment when the injection of a liquid sample into the fluid handling apparatus 10 in this preferred embodiment and the washing of the interior thereof are carried out, the duplicate descriptions thereof are omitted.

Third Preferred Embodiment

Figure 24:
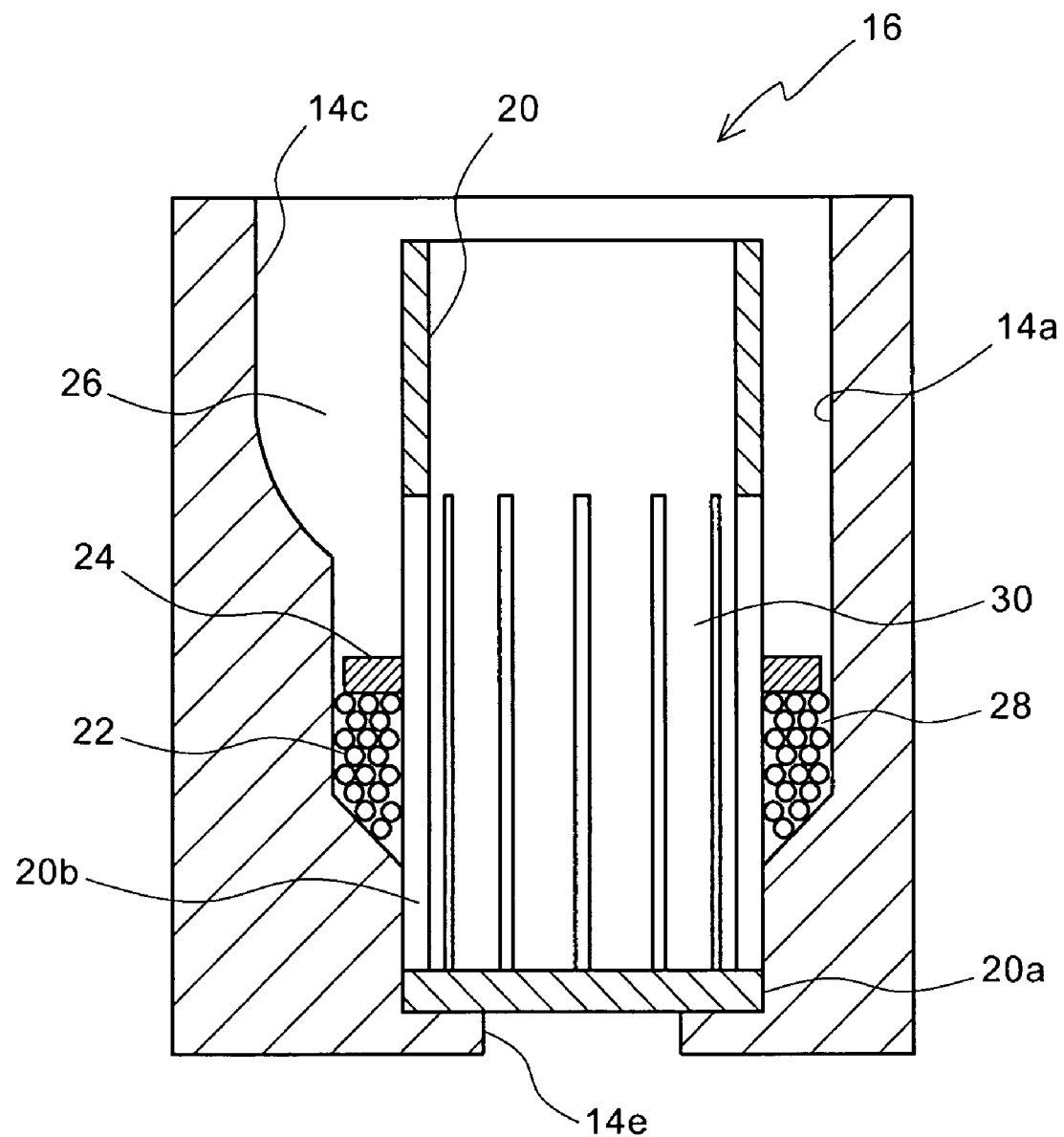
FIG. 24 is a sectional view showing one of fluid handling subassemblies of the third preferred embodiment of a fluid handling apparatus according to the present invention, which corresponds to FIG. 9 showing the state that the lid member is removed from the one of the fluid handling subassemblies in the first preferred embodiment.

FIG. 24 is a sectional view showing one of fluid handling subassemblies 16 of the third preferred embodiment of a fluid handling apparatus according to the present invention, which corresponds to FIG. 9 showing the state that the lid member 25 is removed from the one of the fluid handling subassemblies 16 in the first preferred embodiment. In the fluid handling subassembly 16 in this preferred embodiment, a circular (or another shaped, e.g., rectangular) through hole 14e, which is smaller than the bottom face of the cylindrical member 20, is formed in the bottom face of the small-diameter recessed portion 14b of the mounting recessed portion 14 in place of the fine recessed portion 14d which is formed in the bottom face of the small-diameter recessed portion 14b of the mounting recessed portion 14 of the fluid handling subassembly 16 in the first preferred embodiment. In addition, the lid member 25 of the fluid handling subassembly 16 in the first preferred embodiment is not provided. Since other structural portions of the fluid handling subassembly 16 in this preferred embodiment are the same as those of the fluid handling subassembly 16 in the first preferred embodiment, the same reference numbers are given to the same structural portions as those of the fluid handling subassembly 16 in the first preferred embodiment to omit the duplicate descriptions thereof. In addition, since the flow of liquid is the same as that in the first preferred embodiment when the injection of a liquid sample into the fluid handling apparatus 10 in this preferred embodiment and the washing of the interior thereof are carried out, the duplicate descriptions thereof are omitted.

Figure 25:
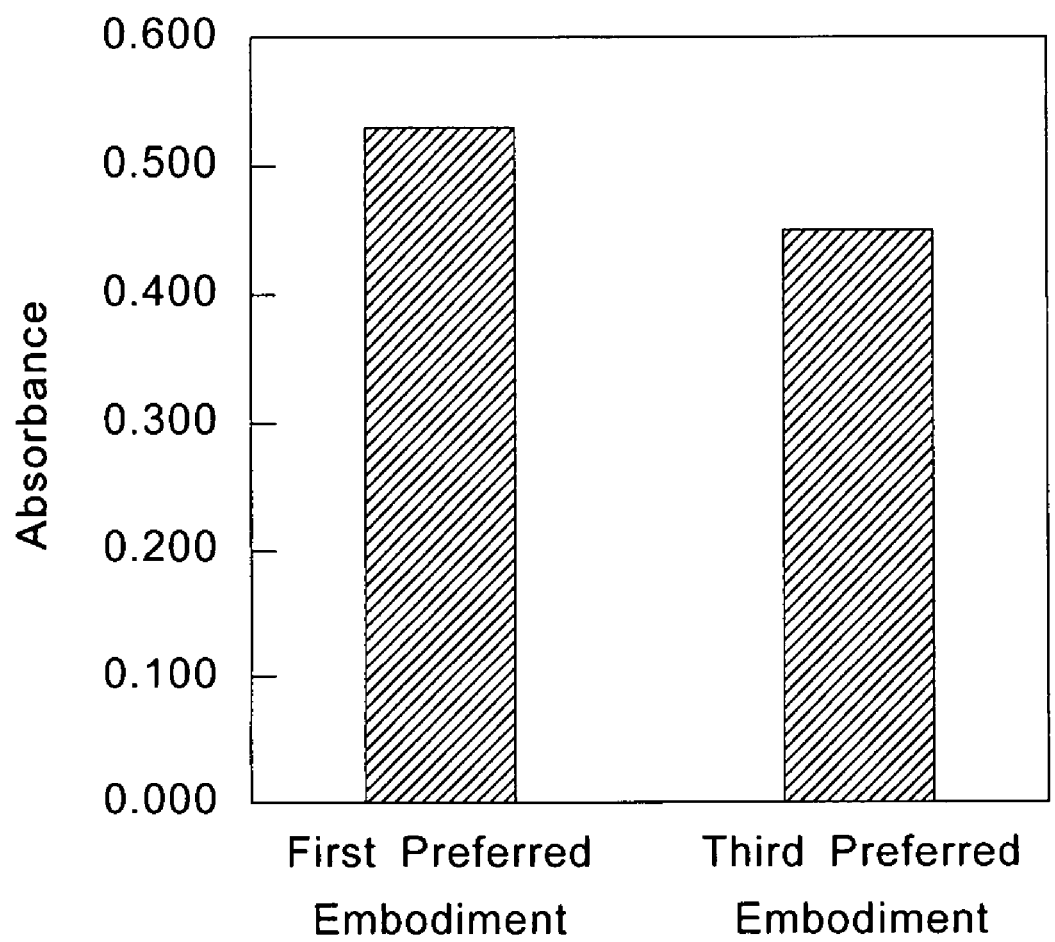
FIG. 25 is a graph showing the results of measurements of blank values in the measurements of absorbance using the fluid handling subassemblies in the first and third preferred embodiments.

In the fluid handling subassembly 16 in the above described first preferred embodiment, the fine recessed portion 14d is formed in the bottom face of the small-diameter recessed portion 14b of the mounting recessed portion 14 to form a gap for preventing the occurrence of interference fringe between the bottom face of the cylindrical member 20 and the bottom face of the mounting recessed portion 14 when the cylindrical member 20 is fitted into the small-diameter recessed portion 14b. However, when the fluid handling apparatus 10 in the first preferred embodiment is used for carrying out a method, such as ELISA, if the detection of a target substance is carried out by the determination of absorbance, transmittance is decreased to raise the background value (blank value) in the measurement of absorbance, since the bottom of the fluid handling subassembly 16 has a dual structure which has the bottom of the cylindrical member 20 and the bottom of the mounting recessed portion 14. For that reason, in the fluid handling subassembly 16 in this preferred embodiment, the through hole 14e serving as a light transmitting opening is formed in the bottom face of the small-diameter recessed portion 14b of the mounting recessed portion 14 to prevent the blank value (background value) from rising during the measurement of absorbance. In order to confirm this effect, after the fluid handling subassemblies 16 in the first preferred embodiment and this preferred embodiment were used for carrying out ELISA to detect a target substance by the determination of absorbance, each of the fluid handling subassemblies 16 was washed, and then, the same solvent as a reagent was added to each of the fluid handling subassemblies 16 to measure a blank value in the measurement of absorbance with light having a wavelength of 450 nm. As a result, as shown in FIG. 25, it was found that the blank value was decreased to 0.45 in this preferred embodiment although the blank value was 0.53 in the first preferred embodiment.

Fourth Preferred Embodiment

Figure 26:
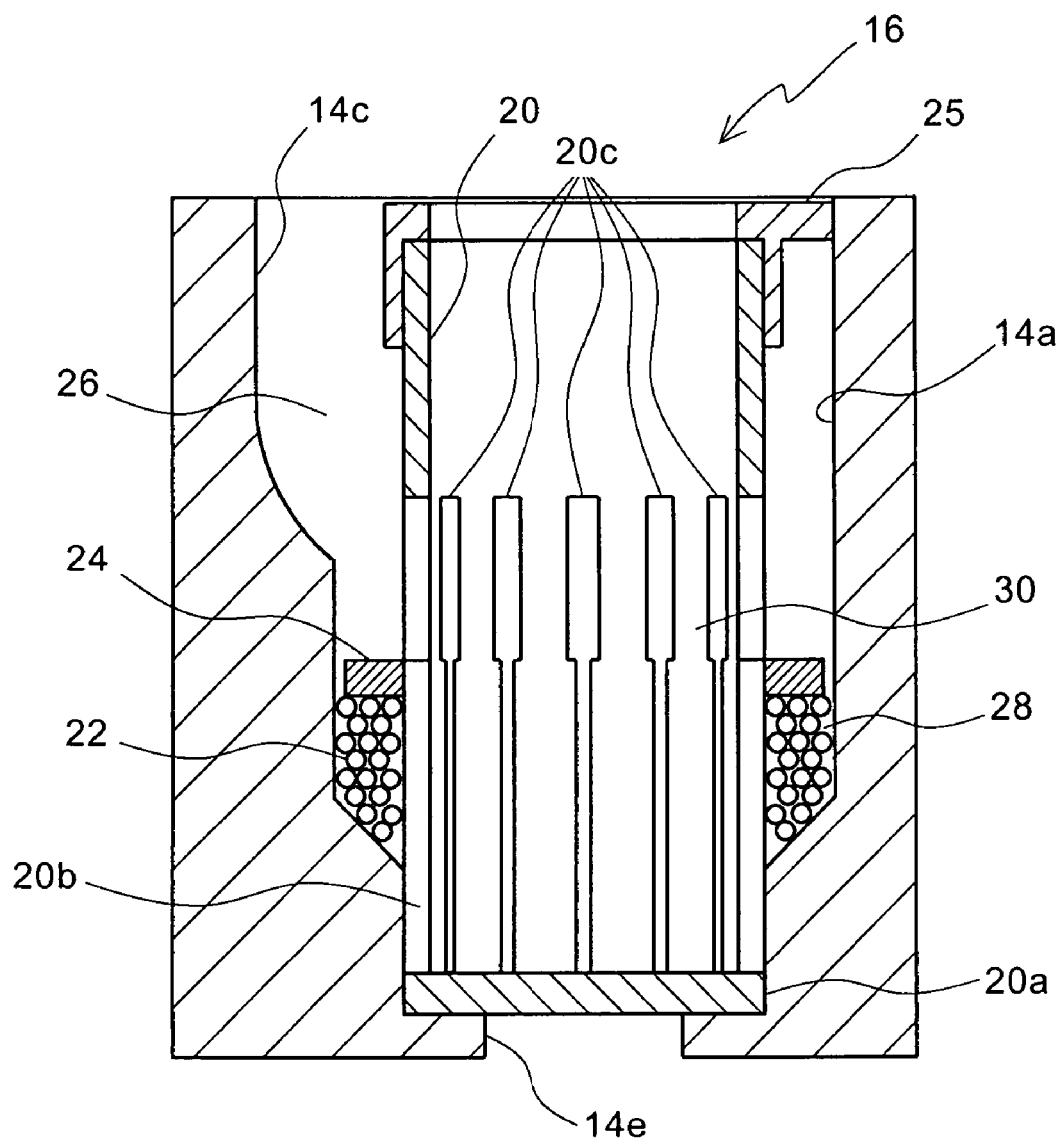
FIG. 26 is a sectional view showing one of fluid handling subassemblies of the fourth preferred embodiment of a fluid handling apparatus according to the present invention, which corresponds to FIG. 7 showing the one of the fluid handling subassemblies in the first preferred embodiment.

FIG. 26 is a sectional view showing one of fluid handling subassemblies 16 of the fourth preferred embodiment of a fluid handling apparatus according to the present invention, which corresponds to FIG. 7 showing the one of the fluid handling subassemblies 16 in the first preferred embodiment. In the fluid handling subassembly 16 in this preferred embodiment, a circular (or another shaped, e.g., rectangular) through hole 14e, which is smaller than the bottom face of the cylindrical member 20, is formed in the bottom face of the small-diameter recessed portion 14b of the mounting recessed portion 14 in place of the fine recessed portion 14d which is formed in the bottom face of the small-diameter recessed portion 14b of the mounting recessed portion 14 of the fluid handling subassembly 16 in the first preferred embodiment. In addition, the upper portion of each of the slits 20b of the cylindrical member 20 of the fluid handling subassembly 16 in the first preferred embodiment (the upper portion of each of the slits 20b above the partition plate 24 when the fluid handling subassembly 16 is mounted in the mounting recessed portion 14) is widened to be formed as a widened portion 20c. Since other structural portions of the fluid handling subassembly 16 in this preferred embodiment are the same as those of the fluid handling subassembly 16 in the first preferred embodiment, the same reference numbers are given to the same structural portions as those of the fluid handling subassembly 16 in the first preferred embodiment to omit the duplicate descriptions thereof. Furthermore, the width of the widened portion 20c of each of the slits 20b of the cylindrical member 20 of the fluid handling apparatus 10 in this preferred embodiment is set as follows. That is, similar to the fluid handling apparatus 10 in the first preferred embodiment, when a liquid sample is injected to the fluid handling apparatus 10 in this preferred embodiment, the liquid sample fed into the fluidized section 28 from the fluidized section inlets (the cut-out portions of the partition plate 24) and the liquid sample fed into the slits 20b (including the widened portions 20c) are extended so as to be filled in the whole fluidized section 28, and the liquid sample is extended in the whole slits 20b (including the widened portions 20c) due to capillarity. Until this state, the liquid sample is not fed into the fluid housing chamber 30 by the surface tension of the liquid sample in the slits 20b (including the widened portions 20c). However, unlike the fluid handling apparatus 10 in the first preferred embodiment, when the fluid handling apparatus 10 in this preferred embodiment is washed, if a larger quantity of washing solution than the quantity of the liquid sample during the injection of the liquid sample is fed into the fluid handling apparatus 10 at a time, the washing solution in the injecting section 26 is fed directly into the fluid housing chamber 30 via the widened portions 20c of the slits 20b. By thus forming the widened portions 20c in the slits 20b, the dirty washing solution discharged above the partition plate 24 from the fluidized section 28 during washing can be smoothly fed into the fluid housing chamber 30 while being prevented from returning to the fluidized section 28, so that it is possible to decrease the quantity of washing residual in the fluidized section 28.

Figure 27:
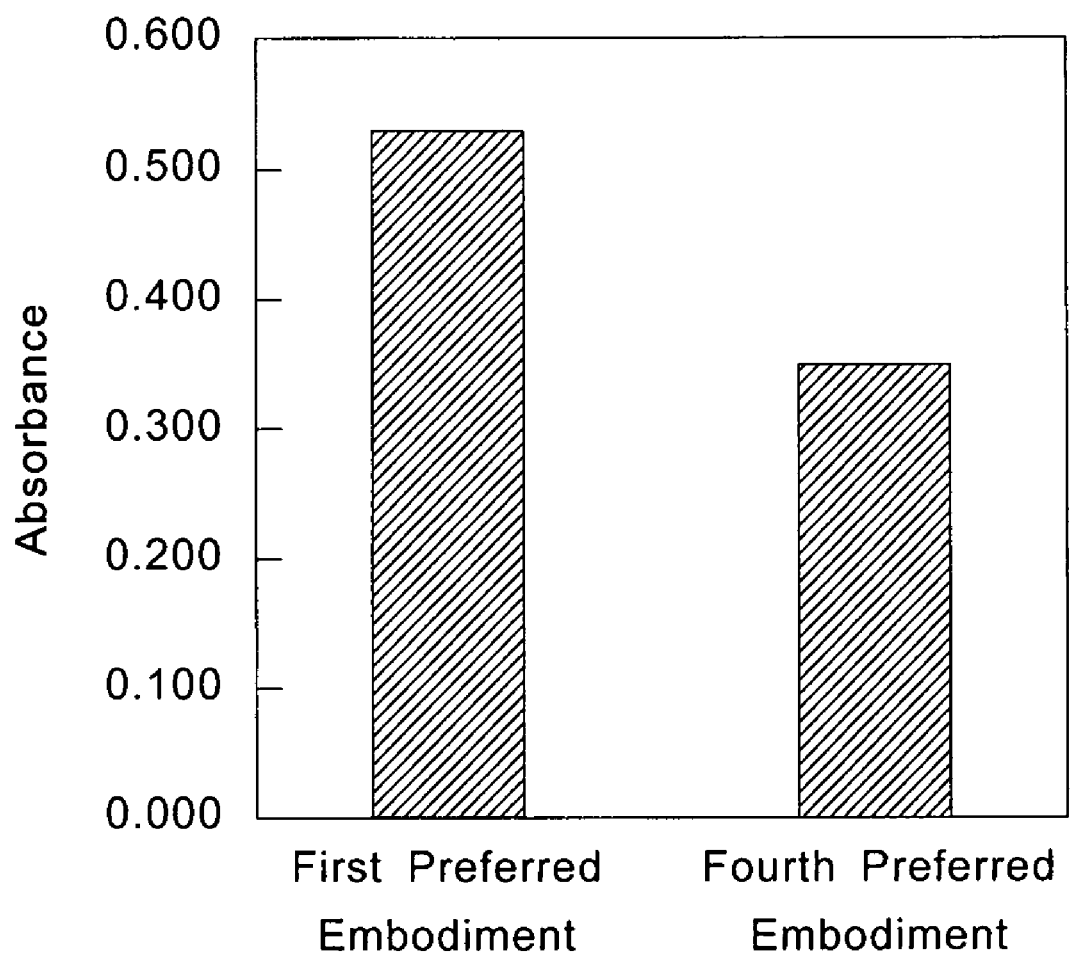
FIG. 27 is a graph showing the results of measurements of blank values in the measurements of absorbance using the fluid handling subassemblies in the first and fourth preferred embodiments.

Also in the fluid handling apparatus 16 in this preferred embodiment similar to the fluid handling apparatus 16 in the above described third preferred embodiment, the through hole 14e serving as a light transmitting opening is formed in the bottom face of the small-diameter recessed portion 14b of the mounting recessed portion 14 to prevent the blank value (background value) from rising during the measurement of absorbance. In order to confirm this effect, after the fluid handling subassemblies 16 in the first preferred embodiment and this preferred embodiment were used for carrying out ELISA to detect a target substance by the determination of absorbance, each of the fluid handling subassemblies 16 was washed, and then, the same solvent as a reagent was added to each of the fluid handling subassemblies 16 to measure a blank value in the measurement of absorbance with light having a wavelength of 450 nm. As a result, as shown in FIG. 27, it was found that the blank value was decreased to 0.35 in this preferred embodiment although the blank value was 0.53 in the first preferred embodiment. Thus, in this preferred embodiment, the blank value can be lower than 0.45 in the third preferred embodiment, so that the blank value can be further decreased by forming the widened portions 20c in the slits 20b. That is, in this preferred embodiment, by thus forming the widened portions 20c in the slits 20b, the dirty washing solution discharged above the partition plate 24 from the fluidized section 28 during washing can be smoothly fed into the fluid housing chamber 30 while being prevented from returning to the fluidized section 28, so that it is possible to decrease the quantity of washing residual in the fluidized section 28. Therefore, the blank value can be lower than that in the third preferred embodiment.

In the fluid handling apparatus 10 in the first through forth preferred embodiments, the large number of beads 22 are filled in the fluidized section 28 to increase the surface area of the inner surface of the passage in the fluidized section 28. Therefore, when the fluid handling apparatus 10 is used as a sample analyzing apparatus, if the surface of each of the beads 22 is utilized as a supporting surface (a reaction surface) for supporting thereon a capturing material, it is possible to increase the surface area of the supporting surface (the reaction surface) for the capturing material to increase the contact area with fluid. If liquid is allowed to continuously flow on the large reaction surface, it is possible to enhance the efficiency of reaction, and it is possible to shorten the reaction time and improve the sensitivity of measurement. Furthermore, even if a porous material having continuous holes coated with a capturing material is arranged in the fluidized section 28 in place of the beads 22, the same advantageous effects can be obtained.

In the fluid handling apparatus 10 in the above described first through fourth preferred embodiments, if the fluid handling subassemblies 16 are mounted on each of the fluid handling subassemblies supporting members 13 of the apparatus body 12, a fluid handling unit, on which the plurality of fluid handling subassemblies 16 are arranged at regular intervals in a row, can be mounted on the frame 11 of the apparatus body 12. Since the fluid handling unit can be thus mounted on the frame 11 every row, it is possible to easily handle the fluid handling apparatus 10.

In the fluid handling apparatus 10 in the above described first through fourth preferred embodiments, when a washing solution 34 is injected into the fluid handling subassembly 16, the most part of the mixed solution 36 of the remaining liquid sample 32 and washing solution 34 is pushed up to the injecting section 26 from the fluidized section 28 filled with the beads 22. Thereafter, when the washing solution 34 is sucked from the fluid handling subassembly 16, the most part of the mixed solution 36 is fed directly into the fluid housing chamber 30 via the slits 20b to be discharged to the outside without passing through the fluidized section 28. Therefore, it is possible to prevent the mixed solution 36 to contact and adhere to the beads 22 in the fluidized section 28 again when the washing solution 34 is sucked, so that it is possible to efficiently wash the interior of the fluid handling subassembly 16 to improve the accuracy of analysis.

While the present invention has been disclosed in terms of the preferred embodiment in order to facilitate better understanding thereof, it should be appreciated that the invention can be embodied in various ways without departing from the principle of the invention. Therefore, the invention should be understood to include all possible embodiments and modifications to the shown embodiments which can be embodied without departing from the principle of the invention as set forth in the appended claims.

What is claimed is:

1. A fluid handling apparatus comprising an apparatus body and a plurality of fluid handling subassemblies arranged on the apparatus body, each of the fluid handling subassemblies comprising:
    an injecting section for injecting a fluid;
    a fluidized section for receiving the fluid from the injecting section to allow the fluid to continuously flow downwards;
    a fluid housing chamber for receiving the fluid from the fluidized section;
    a wall portion formed between the fluid housing chamber and the injecting section and between the fluid housing chamber and the fluidized section;
    an opening, formed in the wall portion wherein said opening is a slit which passes through said wall portion, for allowing the fluid to enter the fluid housing chamber; and
    a surface-area increasing means, arranged in the fluidized section, for increasing an area of a contact surface with the fluid in the fluidized section,
    wherein the opening extends from a lower end, which is positioned in the vicinity of the lower end of the fluidized section, to an upper end, which is higher than the upper end of the fluidized section, for allowing the injecting section and the fluidized section to be communicated with the fluid housing chamber.

2. A fluid handling apparatus as set forth in claim 1, wherein said slit has an upper portion having a width which is wider than that of a lower portion of the slit.

3. A fluid handling apparatus as set forth in claim 1, wherein said opening has a lower end arranged at a level which is substantially equal to a bottom face of said fluid housing chamber.

4. A fluid handling apparatus as set forth in claim 1, wherein said apparatus body comprises a frame and a plurality of supporting members which are arranged on the frame so as to be substantially parallel to each other, each of the supporting members having a plurality of recessed portions which are arranged at regular intervals in a row, and each of said plurality of fluid handling subassemblies being mounted in a corresponding one of the recessed portions.

5. A fluid handling apparatus as set forth in claim 1, wherein said fluidized section is arranged so as to surround said fluid housing chamber.

6. A fluid handling apparatus as set forth in claim 4, wherein each of said plurality of recessed portions comprises an upper recessed portion, and a lower recessed portion which is formed in a bottom face of said upper recessed portion,
    said fluidized section being formed between a partition wall member, which is inserted into each of said plurality of recessed portions, and said upper recessed portion, and
    said fluid housing chamber being surrounded by said partition wall member.

7. A fluid handling apparatus as set forth in claim 6, wherein an extended recessed portion for extending said upper cylindrical recessed portion in substantially horizontal directions is formed in each of said plurality of recessed portions.

8. A fluid handling apparatus as set forth in claim 1, wherein said surface-area increasing means comprises a large number of fine particles filled in said fluidized section.

9. A fluid handling apparatus as set forth in claim 1, wherein said surface-area increasing means is a porous material.

10. A fluid handling apparatus as set forth in claim 1, wherein a liquid injected into said injecting section flows in said fluidized section and said opening due to capillarity.

11. A fluid handling unit comprising a supporting member and a plurality of fluid handling subassemblies which are arranged on the supporting member at regular intervals in a row, each of said fluid handling subassemblies comprising:

an injecting section for injecting a fluid;

a fluidized section for receiving the fluid from the injecting section to allow the fluid to continuously flow downwards;

a fluid housing chamber, formed so as to be surrounded by said fluidized section, for receiving the fluid from the fluidized section;

a wall portion formed between the fluid housing chamber and the injecting section and between the fluid housing chamber and the fluidized section;

an opening, formed in the wall portion wherein said opening is a slit which passes through said wall portion, for allowing the fluid to enter the fluid housing chamber; and a surface-area increasing means, arranged in the fluidized section, for increasing an area of a contact surface with the fluid in the fluidized section, wherein the opening extends from a lower end, which is positioned in the vicinity of the lower end of the fluidized section, to an upper end, which is higher than the upper end of the fluidized section, for allowing the injecting section and the fluidized section to be communicated with the fluid housing chamber.

12. A fluid handling unit as set forth in claim 10, wherein said slit has an upper portion having a width which is wider than that of a lower portion of the slit.

13. A fluid handling unit as set forth in claim 10, wherein said opening has a lower end arranged at a level which is substantially equal to a bottom face of said fluid housing chamber.

14. A fluid handling unit as set forth in claim 10, wherein said surface-area increasing means comprises a large number of fine particles filled in said fluidized section.

15. A fluid handling unit as set forth in claim 10, wherein said surface-area increasing means is a porous material.

16. A fluid handling unit as set forth in claim 10, wherein a liquid injected into said injecting section flows in said fluidized section and said opening due to capillarity.

* * * * *